United States Patent
Koda et al.

(10) Patent No.: US 11,406,747 B2
(45) Date of Patent: Aug. 9, 2022

(54) EXTRACORPOREAL CIRCULATION APPARATUS AND METHOD OF DISCHARGING BUBBLES THEREFROM

(71) Applicant: Nikkiso Company Limited, Tokyo (JP)

(72) Inventors: Shunichi Koda, Shizuoka (JP); Shunsuke Kawamura, Shizuoka (JP); Shingo Okamoto, Shizuoka (JP)

(73) Assignee: Nikkiso Company Limited, Tokyo (JP)

( * ) Notice: Subject to any disclaimer, the term of this patent is extended or adjusted under 35 U.S.C. 154(b) by 398 days.

(21) Appl. No.: 16/811,042

(22) Filed: Mar. 6, 2020

(65) Prior Publication Data
US 2020/0206406 A1 Jul. 2, 2020

Related U.S. Application Data

(63) Continuation of application No. PCT/JP2018/033151, filed on Sep. 7, 2018.

(30) Foreign Application Priority Data

Sep. 7, 2017 (JP) .............................. JP2017-172561

(51) Int. Cl.
*A61M 1/36* (2006.01)
*A61M 1/26* (2006.01)
(Continued)

(52) U.S. Cl.
CPC ........ *A61M 1/3643* (2013.01); *A61M 1/3624* (2013.01); *F04B 43/1238* (2013.01); *F04B 13/00* (2013.01)

(58) Field of Classification Search
CPC .............. A61M 1/3624; A61M 1/3643; A61M 1/3644; A61M 1/3649; F04B 13/00; F04B 43/1238
See application file for complete search history.

(56) References Cited

U.S. PATENT DOCUMENTS 3,046,788 A 7/1962 Laimins
4,090,404 A 5/1978 Dupont et al.
(Continued)

FOREIGN PATENT DOCUMENTS

| CN | 1405450 A | 3/2003 |
| EP | 1666078 A2 | 6/2006 |

(Continued)

OTHER PUBLICATIONS

Potentially related U.S. Appl. No. 15/292,404, filed Oct. 13, 2016, U.S. Pat. No. 10,532,143 dated Jan. 14, 2020.
(Continued)

*Primary Examiner* — Dirk R Bass
(74) *Attorney, Agent, or Firm* — Young Basile Hanlon & MacFarlane, P.C.

(57) ABSTRACT

An extracorporeal circulation apparatus including a blood circuit including an arterial blood circuit and a venous blood circuit whose proximal ends are connected to a blood purifier, the blood circuit allowing a patient's blood to extracorporeally circulate from a distal end of the arterial blood circuit to a distal end of the venous blood circuit; a discharge unit through which a priming solution supplied into the blood circuit is discharged to an outside; a negative-pressure-generating unit that generates a negative pressure in a region of the blood circuit, the region being filled with the priming solution; and a control unit that controls the negative-pressure-generating unit. The control unit executes a priming step in which the priming solution supplied into the blood circuit is discharged through the discharge unit while a flow route in the blood circuit is filled with the priming solution; a negative-pressure-generating step in which, after the priming step, a negative pressure is generated in the region by the negative-pressure-generating unit; and a discharge step in which bubbles in the region subjected (Continued)

to the negative pressure generated in the negative-pressure-generating step are caused to flow and are discharged through the discharge unit.

20 Claims, 20 Drawing Sheets

(51) Int. Cl.
   *F04B 13/00* (2006.01)
   *F04B 43/12* (2006.01)

(56) References Cited

U.S. PATENT DOCUMENTS

| | | |
|---|---|---|
| 4,460,355 A | 7/1984 | Layman |
| 4,498,843 A | 2/1985 | Schneider et al. |
| 4,534,756 A | 8/1985 | Nelson |
| 4,558,996 A | 12/1985 | Becker |
| 4,585,399 A | 4/1986 | Baier |
| 4,743,228 A | 5/1988 | Butterfield |
| 4,762,518 A | 8/1988 | Kreinick |
| 4,784,576 A | 11/1988 | Bloom et al. |
| 4,969,808 A | 11/1990 | Tsukada |
| 5,024,099 A | 6/1991 | Lee |
| 5,215,450 A | 6/1993 | Tamari |
| 5,336,051 A | 8/1994 | Tamari |
| 5,356,378 A | 10/1994 | Doan |
| 5,380,172 A | 1/1995 | Ulbing |
| 5,429,483 A | 7/1995 | Tamari |
| 5,501,665 A | 3/1996 | Jhuboo et al. |
| 5,577,891 A | 11/1996 | Loughnane et al. |
| 5,720,721 A | 2/1998 | Dumas et al. |
| 5,813,842 A | 9/1998 | Tamari |
| 5,814,004 A | 9/1998 | Tamari |
| 5,827,223 A | 10/1998 | Butterfield |
| 5,920,054 A | 7/1999 | Uber, III |
| 5,927,951 A | 7/1999 | Tamari |
| 6,039,078 A | 3/2000 | Tamari |
| 6,374,084 B1 | 4/2002 | Fok |
| 6,423,029 B1 | 7/2002 | Elsberry |
| 6,497,680 B1 | 12/2002 | Holst et al. |
| 6,868,720 B2 | 3/2005 | Lobdell et al. |
| 7,004,924 B1 | 2/2006 | Brugger et al. |
| 7,037,092 B2 | 5/2006 | Kagawa et al. |
| 7,462,163 B2 | 12/2008 | Yap et al. |
| 7,935,912 B2 | 5/2011 | Arima et al. |
| 8,011,905 B2 | 9/2011 | Artsyukhovich et al. |
| 9,004,886 B2 | 4/2015 | Beck et al. |
| 9,662,433 B2 | 5/2017 | Matsuo et al. |
| 10,532,143 B2 | 1/2020 | Mochizuki |
| 2001/0004444 A1 | 6/2001 | Haser et al. |
| 2002/0151838 A1 | 10/2002 | Beck et al. |
| 2003/0040700 A1 | 2/2003 | Hickle et al. |
| 2003/0071072 A1 | 4/2003 | Takahashi et al. |
| 2003/0214412 A1 | 11/2003 | Ho et al. |
| 2005/0025647 A1 | 2/2005 | Ortega et al. |
| 2007/0217933 A1 | 9/2007 | Haser et al. |
| 2007/0258838 A1 | 11/2007 | Drake et al. |
| 2008/0154095 A1 | 6/2008 | Stubkjaer et al. |
| 2009/0214365 A1 | 8/2009 | Norman et al. |
| 2010/0049134 A1 | 2/2010 | Schuman, Jr. |
| 2010/0106466 A1 | 4/2010 | Frohlich et al. |
| 2010/0203179 A1 | 8/2010 | Kaushik et al. |
| 2011/0033318 A1 | 2/2011 | Ramirez, Jr. et al. |
| 2011/0130741 A1 | 6/2011 | Miles et al. |
| 2011/0230814 A1 | 9/2011 | Kopperschmidt et al. |
| 2012/0082576 A1 | 4/2012 | Beck et al. |
| 2012/0083737 A1 | 4/2012 | Beck |
| 2014/0219829 A1 | 8/2014 | Matsuo et al. |
| 2015/0217040 A1 | 8/2015 | Matsuo et al. |
| 2015/0238677 A1 | 8/2015 | Akita et al. |
| 2018/0133384 A1 | 5/2018 | Tokunaga et al. |

FOREIGN PATENT DOCUMENTS

| | | |
|---|---|---|
| EP | 1947340 A1 | 7/2008 |
| EP | 2749858 A1 | 7/2014 |
| EP | 2752210 A1 | 7/2014 |
| EP | 3069742 A1 | 9/2016 |
| JP | S56-113083 A | 9/1981 |
| JP | S64-022357 A | 2/1989 |
| JP | H03-001290 U1 | 1/1991 |
| JP | H04-015938 U1 | 1/1992 |
| JP | H08-510812 A | 11/1996 |
| JP | 2003-265601 A | 9/2003 |
| JP | 2004-049494 A | 2/2004 |
| JP | 2004-187990 A | 7/2004 |
| JP | 2005-503202 A | 2/2005 |
| JP | 2007-224909 A | 9/2007 |
| JP | 2008-000425 A | 1/2008 |
| JP | 2008-002388 A | 1/2008 |
| JP | 2008-208808 A | 9/2008 |
| JP | 2008-289635 A | 12/2008 |
| JP | 2009-525770 A | 7/2009 |
| JP | 2009285128 A | 12/2009 |
| JP | 2009297193 A | 12/2009 |
| JP | 2010-188170 A | 9/2010 |
| JP | 2010-190062 A | 9/2010 |
| JP | 2010-273693 A | 12/2010 |
| JP | 2011-030880 A | 2/2011 |
| JP | 2012-192099 A | 10/2012 |
| JP | 2012-192100 A | 10/2012 |
| JP | 2015-092977 A | 5/2015 |
| WO | 1994/028309 A1 | 12/1994 |
| WO | 95/10310 A1 | 4/1995 |
| WO | 97/10013 A1 | 3/1997 |
| WO | 2007/072772 A1 | 6/2007 |
| WO | 2007/093064 A1 | 8/2007 |
| WO | 2010/020380 A1 | 2/2010 |
| WO | 2016/020061 A2 | 2/2016 |

OTHER PUBLICATIONS

Potentially related U.S. Appl. No. 16/811,046, filed Mar. 6, 2020 entitled "Blood Purification Apparatus and Method of Discharging Bubbles Therefrom".

European Search Report for Application No. 18854122.1, dated May 6, 2021.

[Fig. 1]
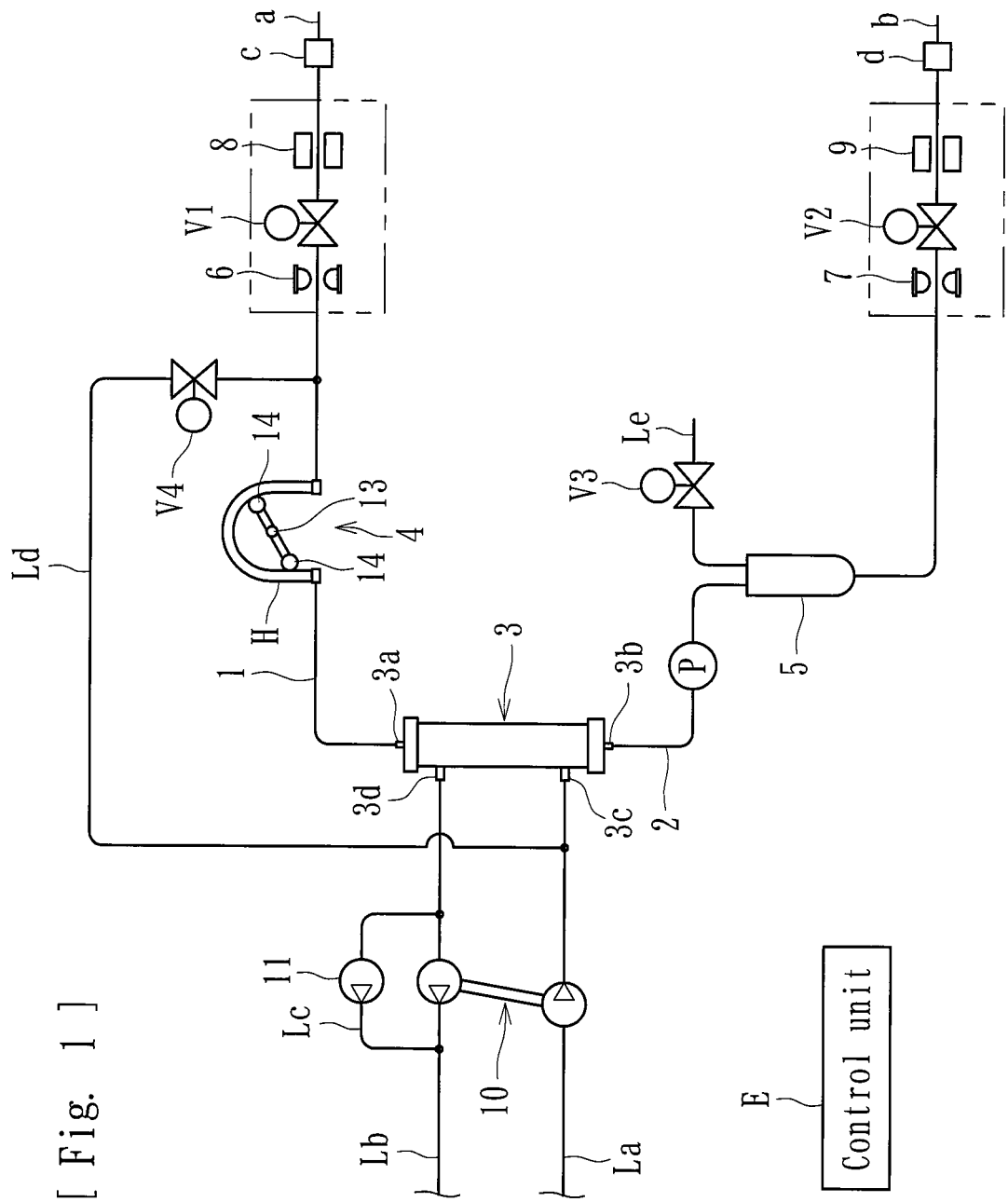

[Fig. 2]
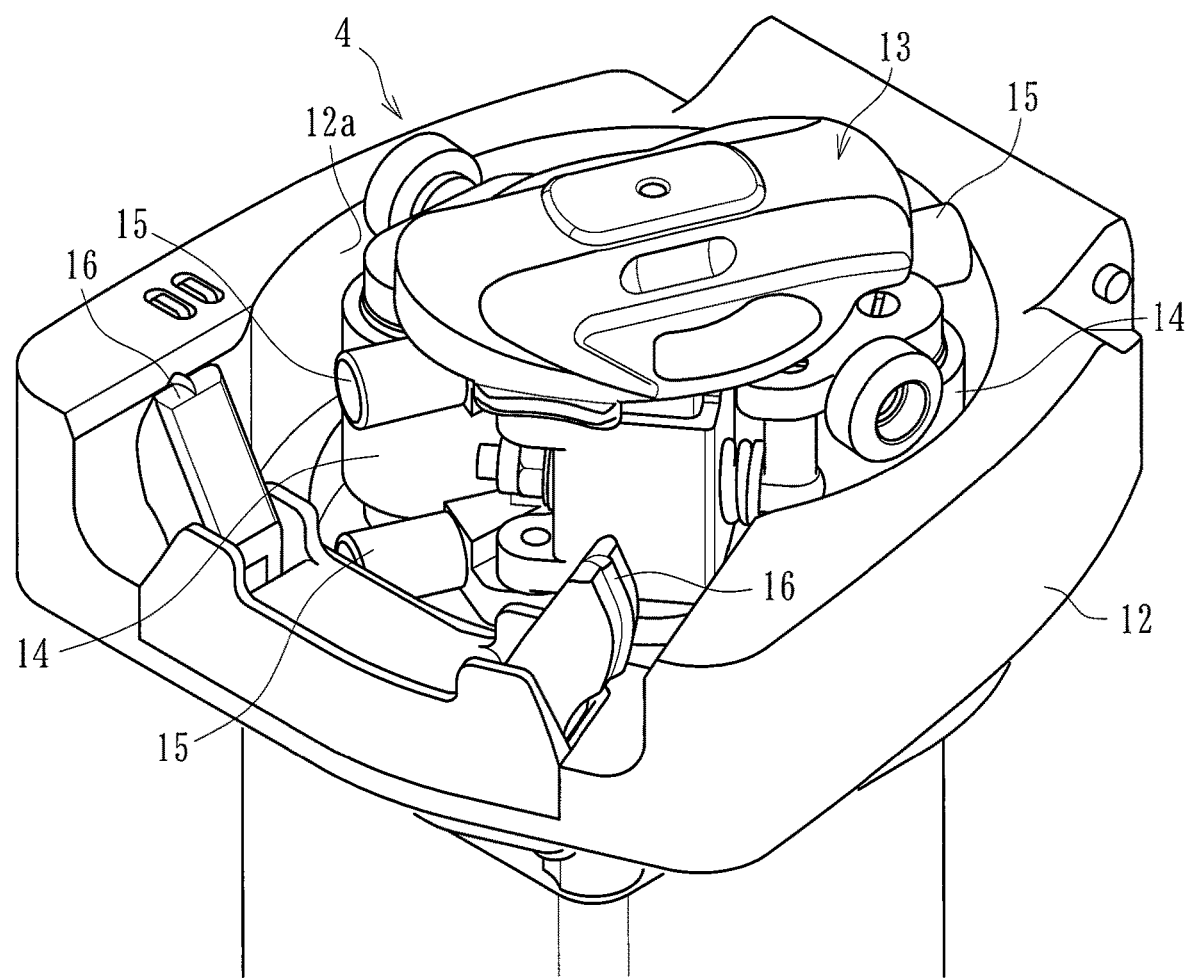

[Fig. 3]
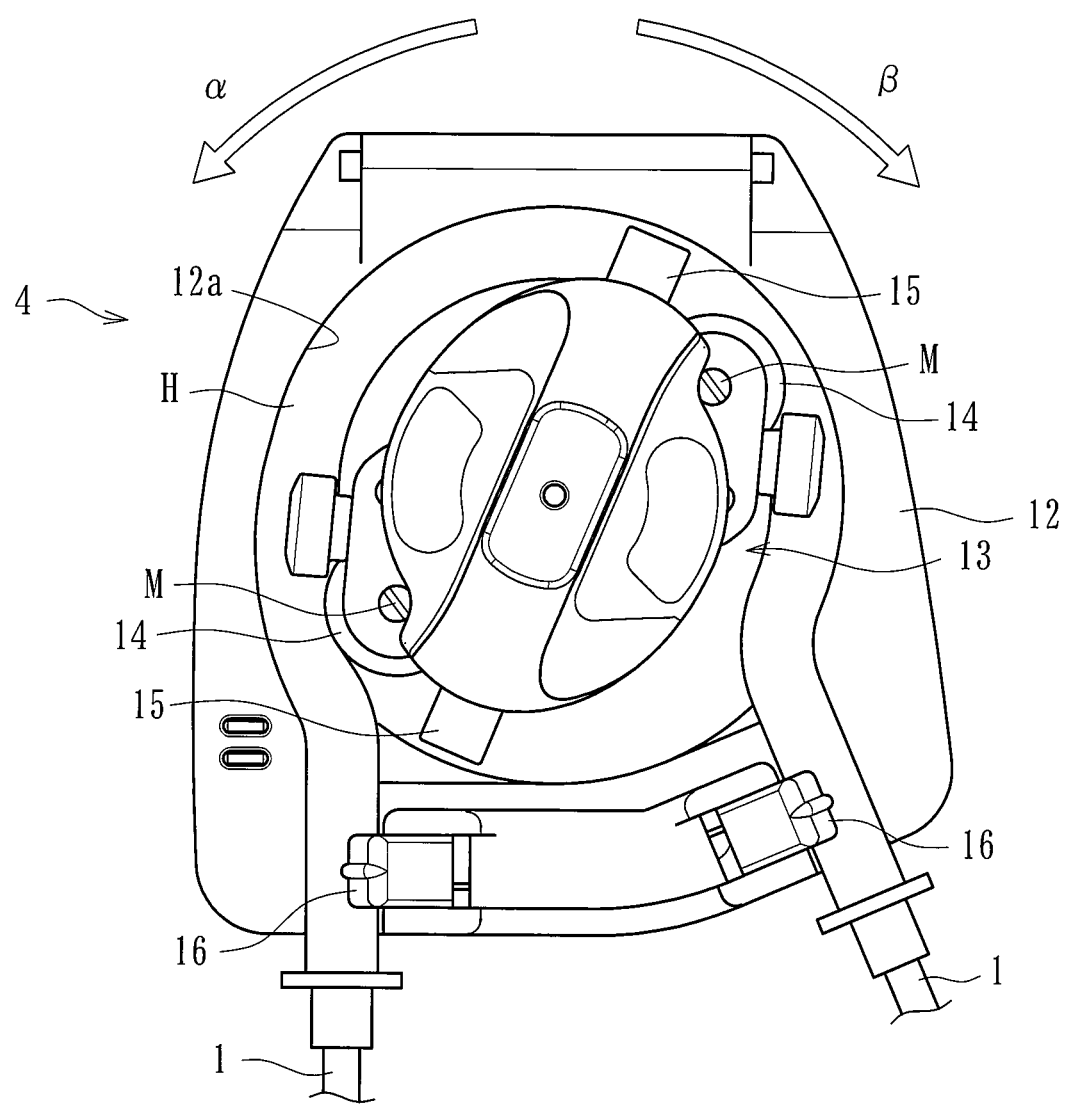

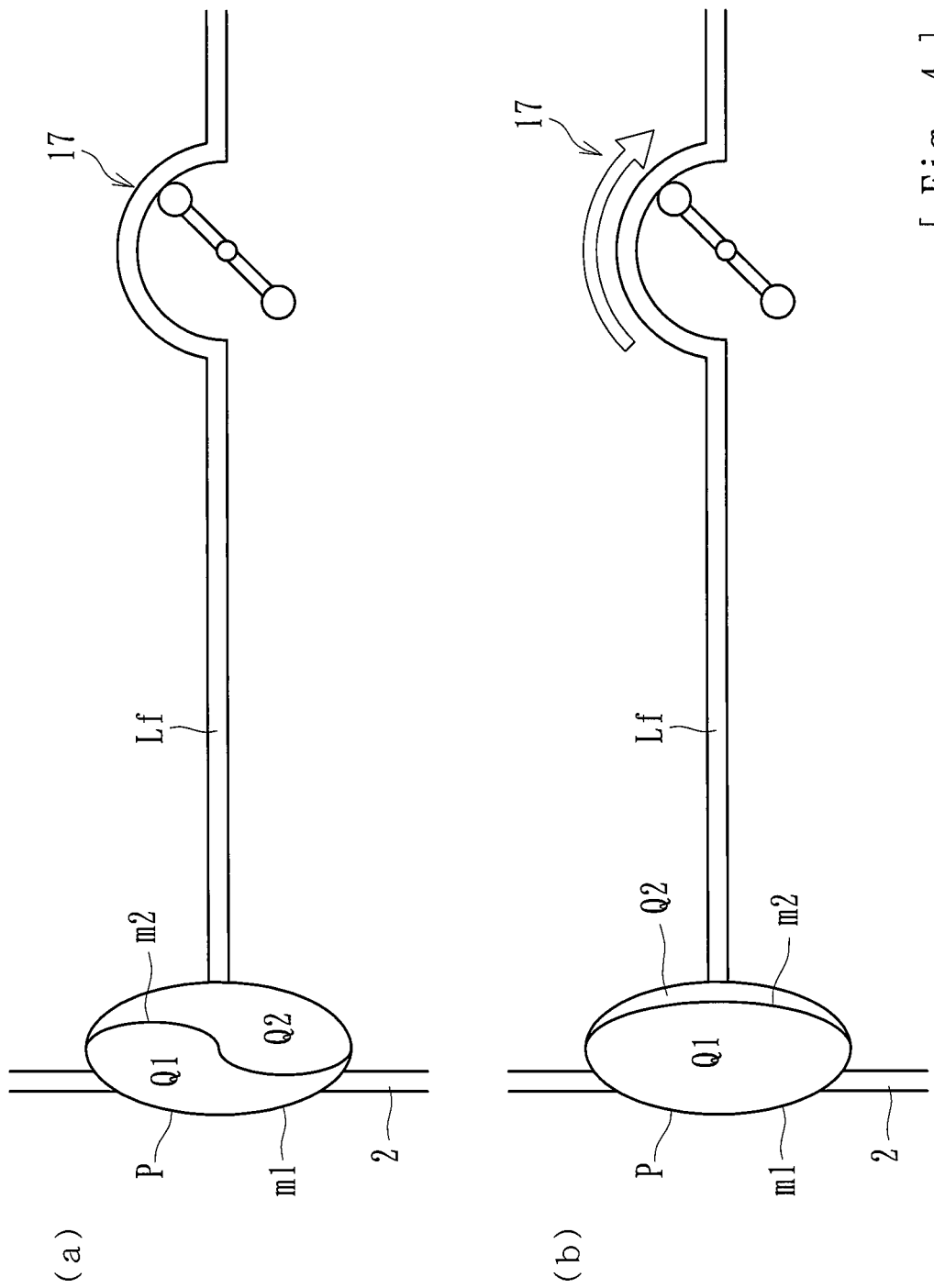

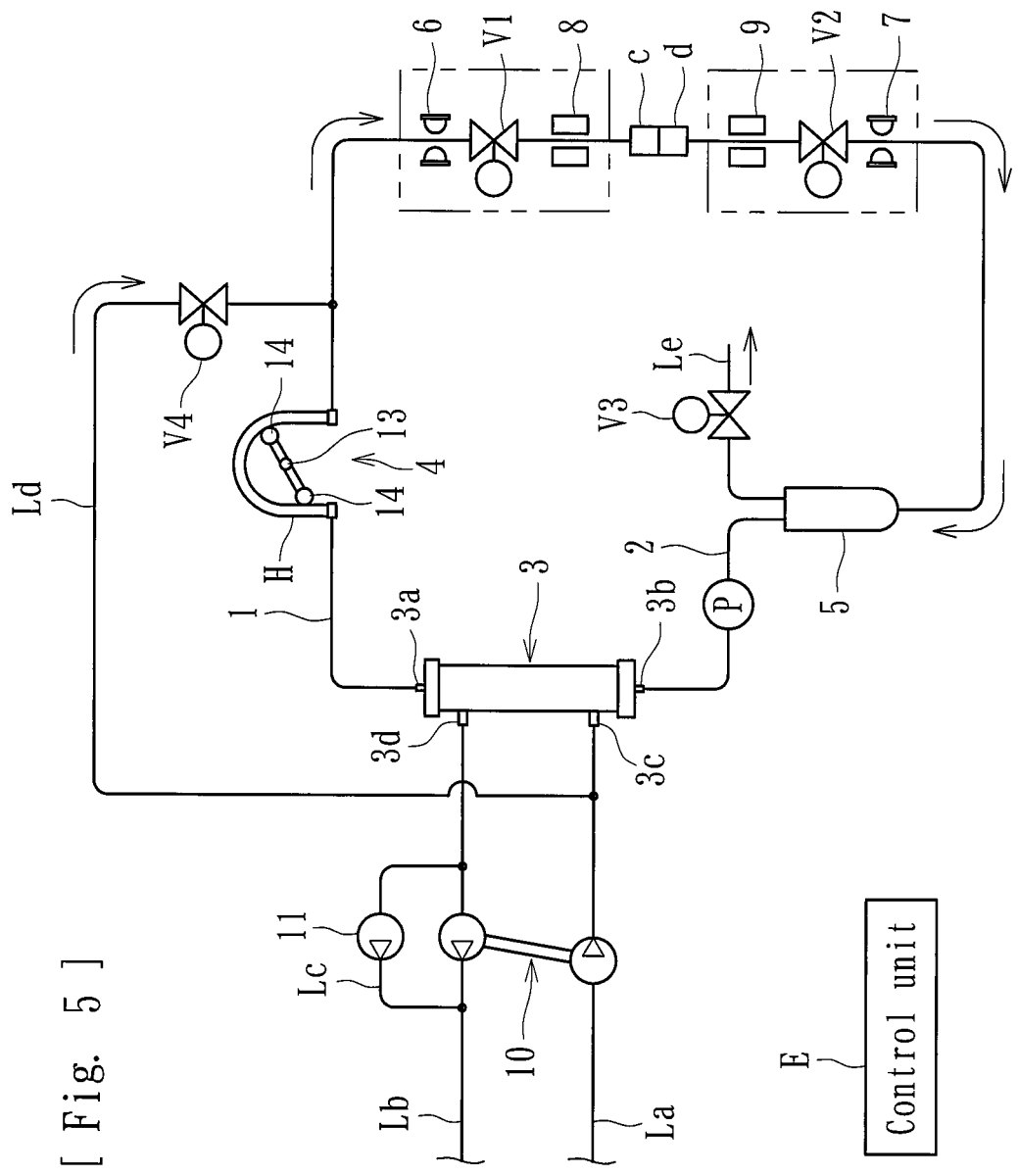
[Fig. 5]

[Fig. 6]
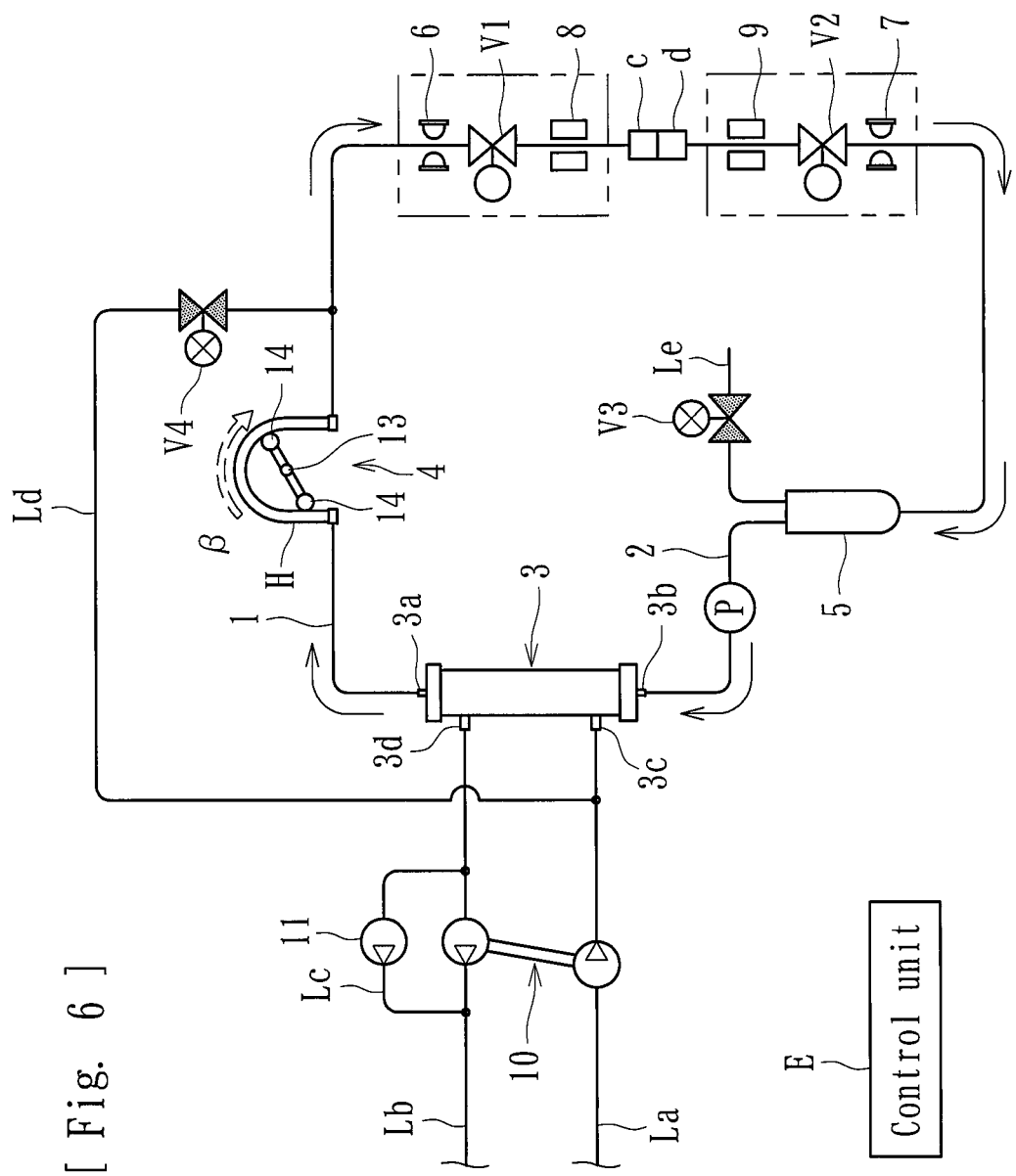

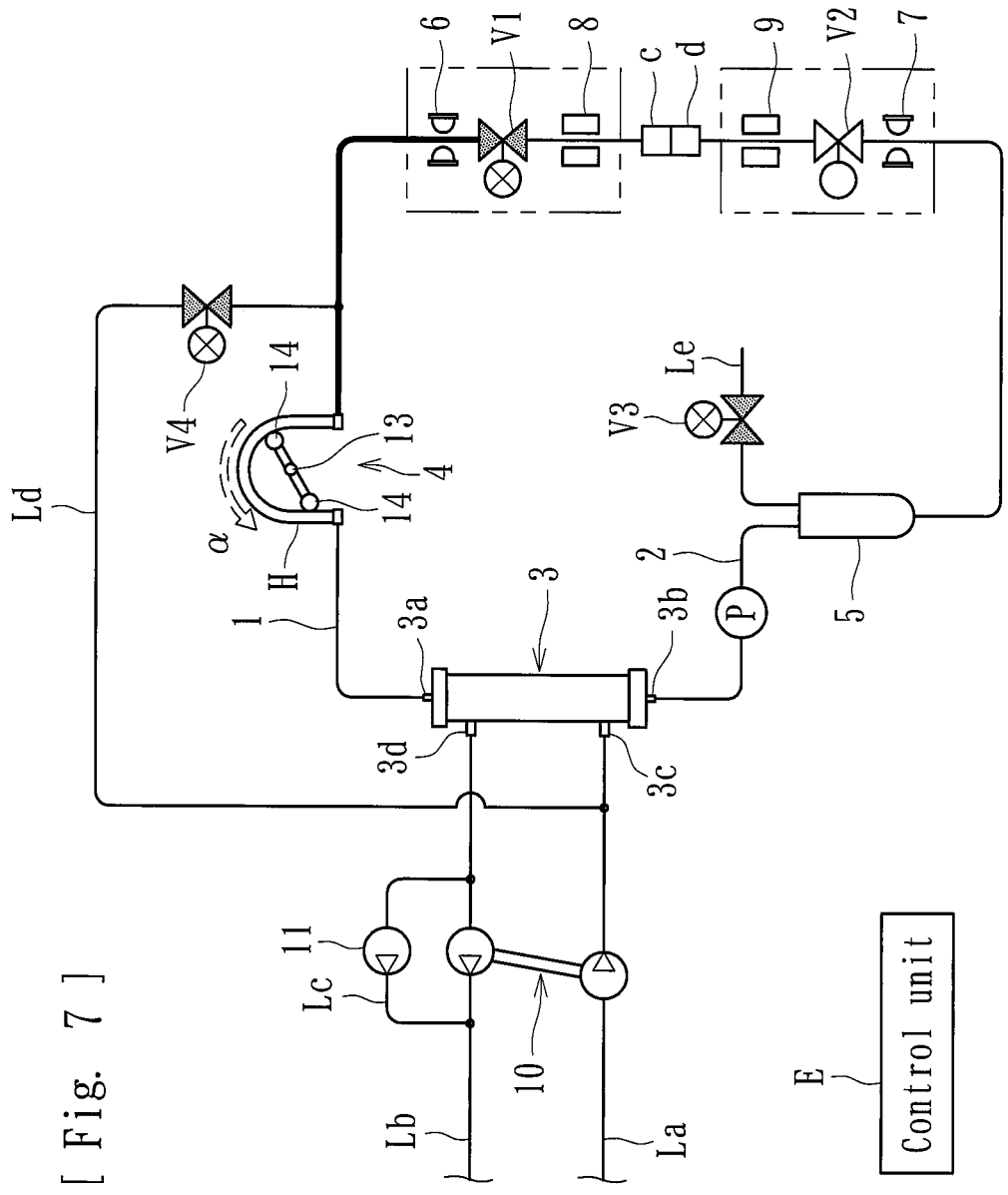

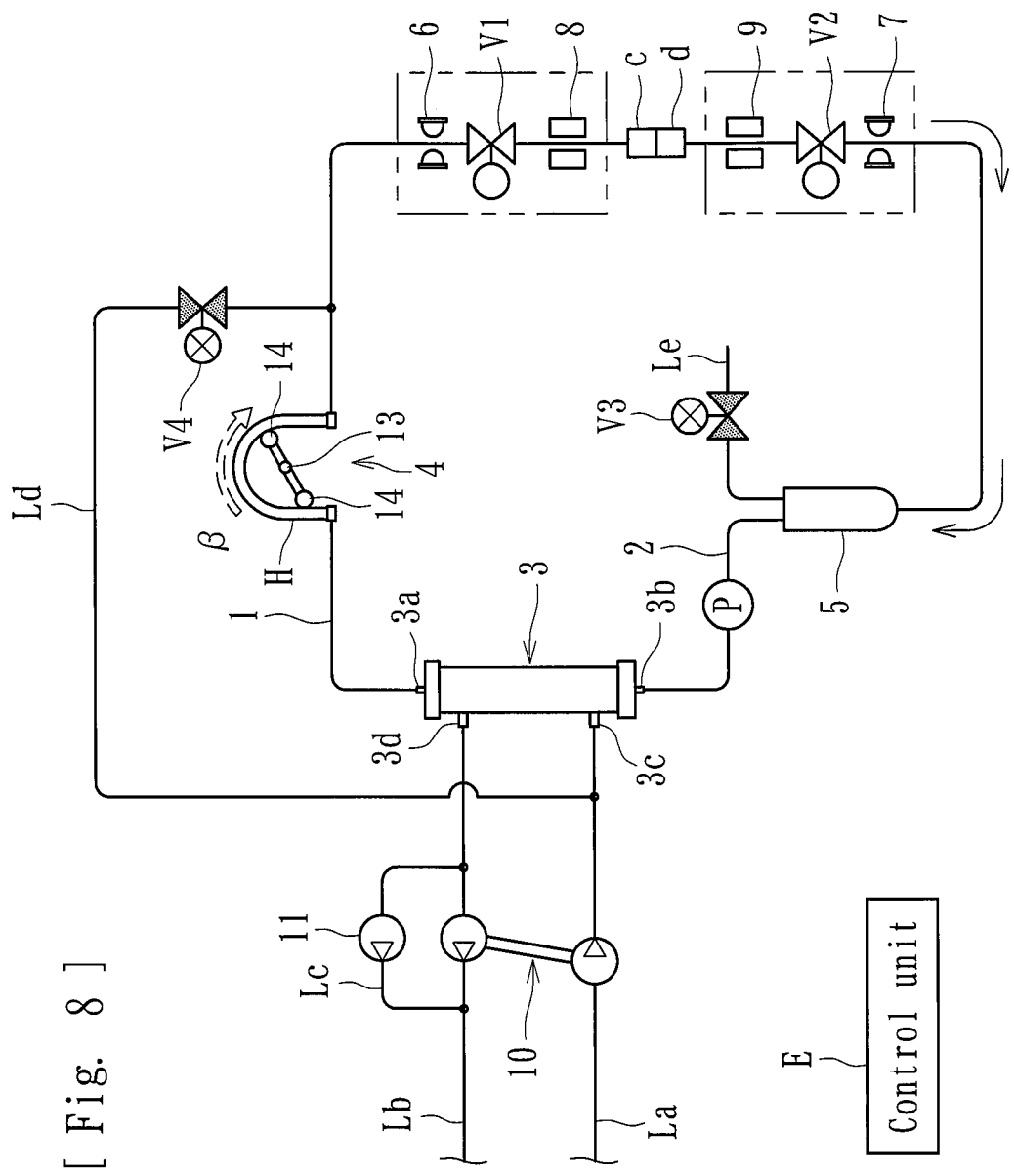
[Fig. 8]

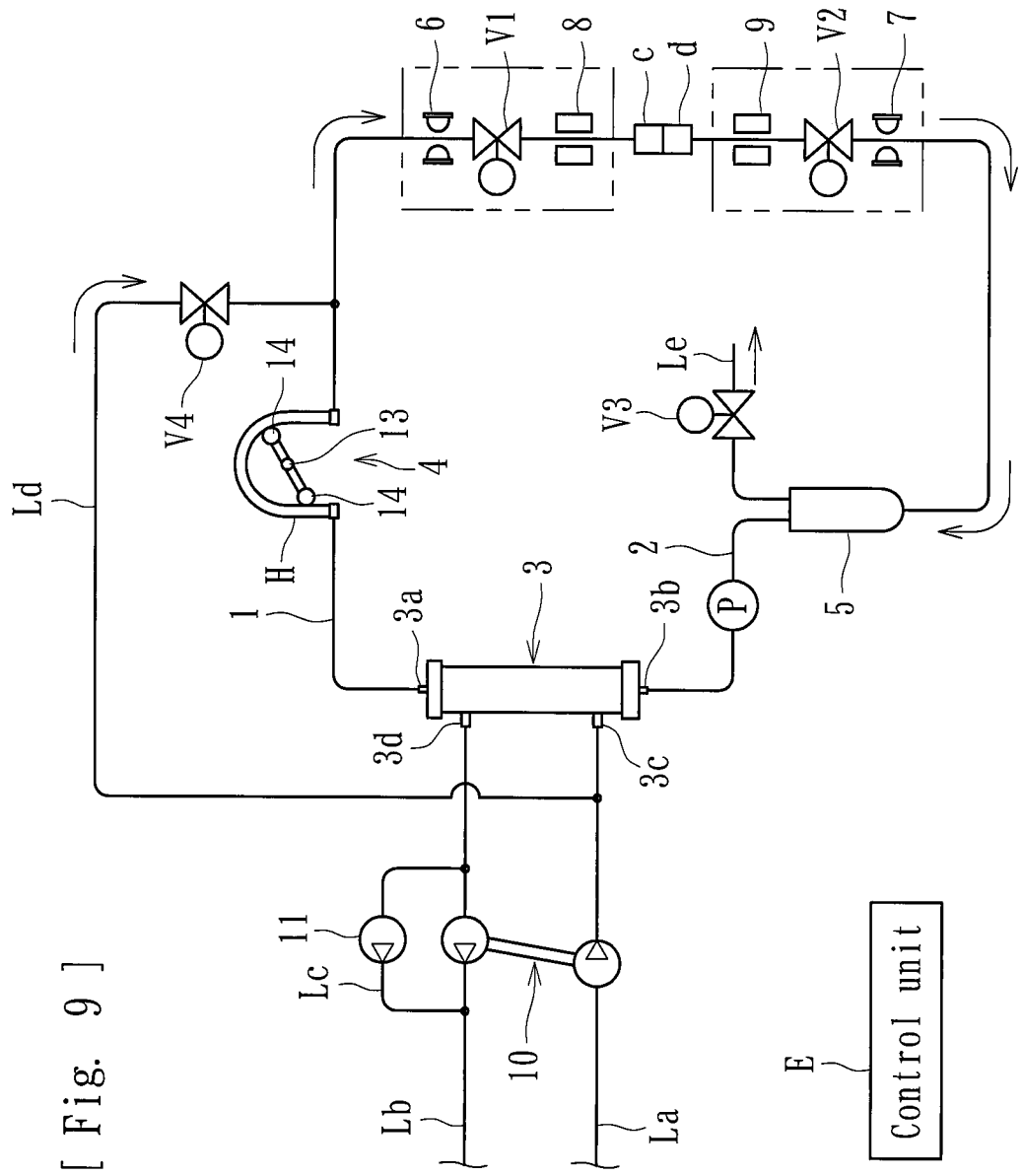
[Fig. 9]

[ Fig. 10 ]
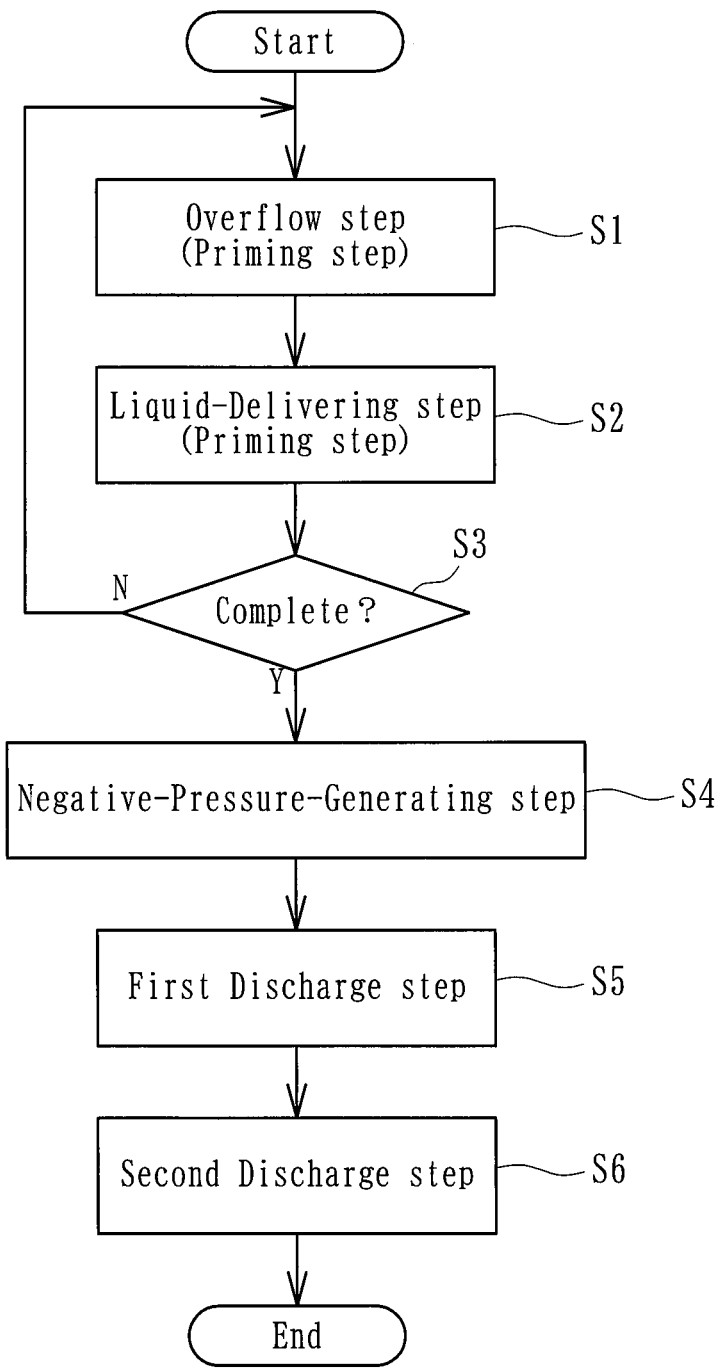

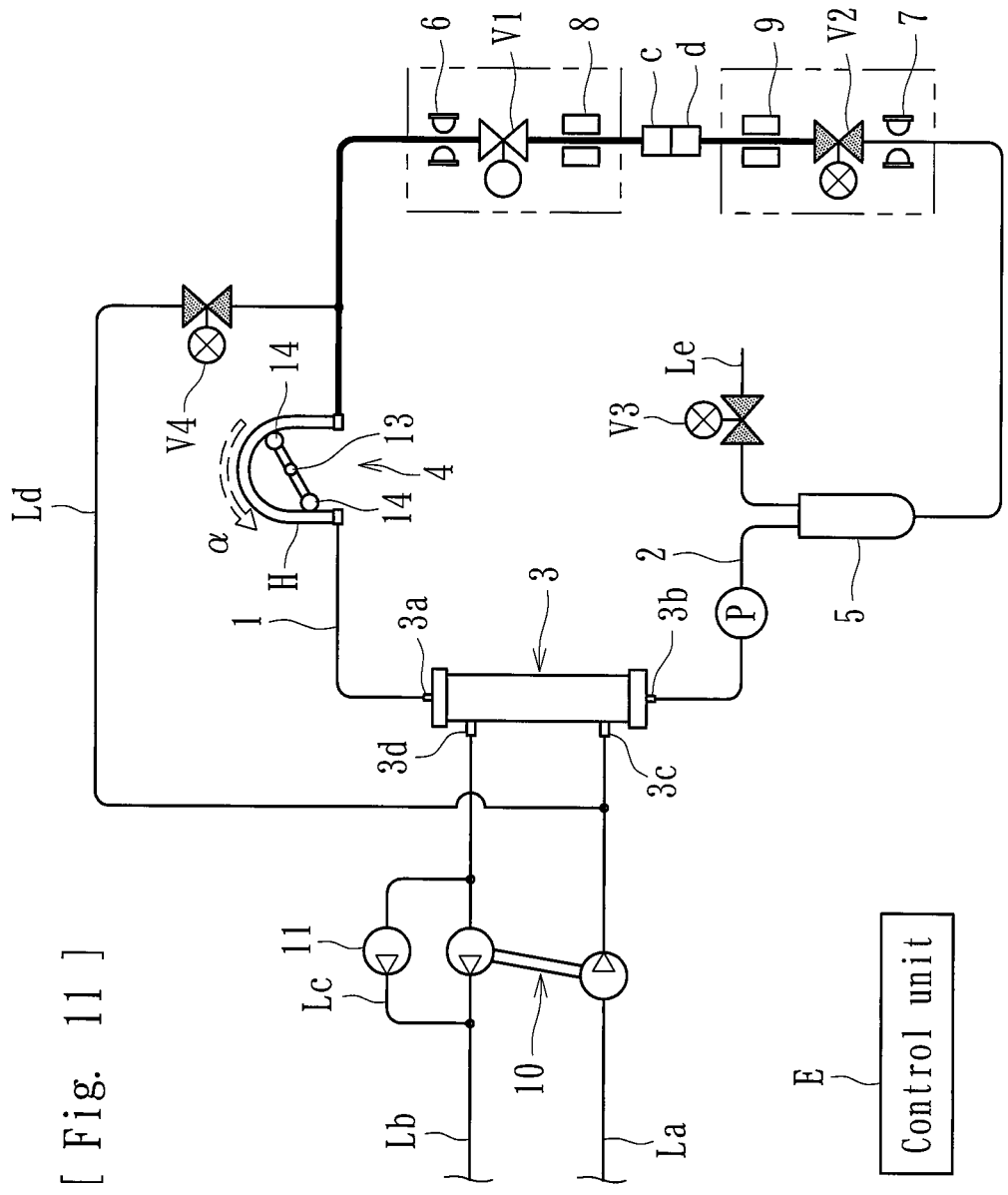
[Fig. 11]

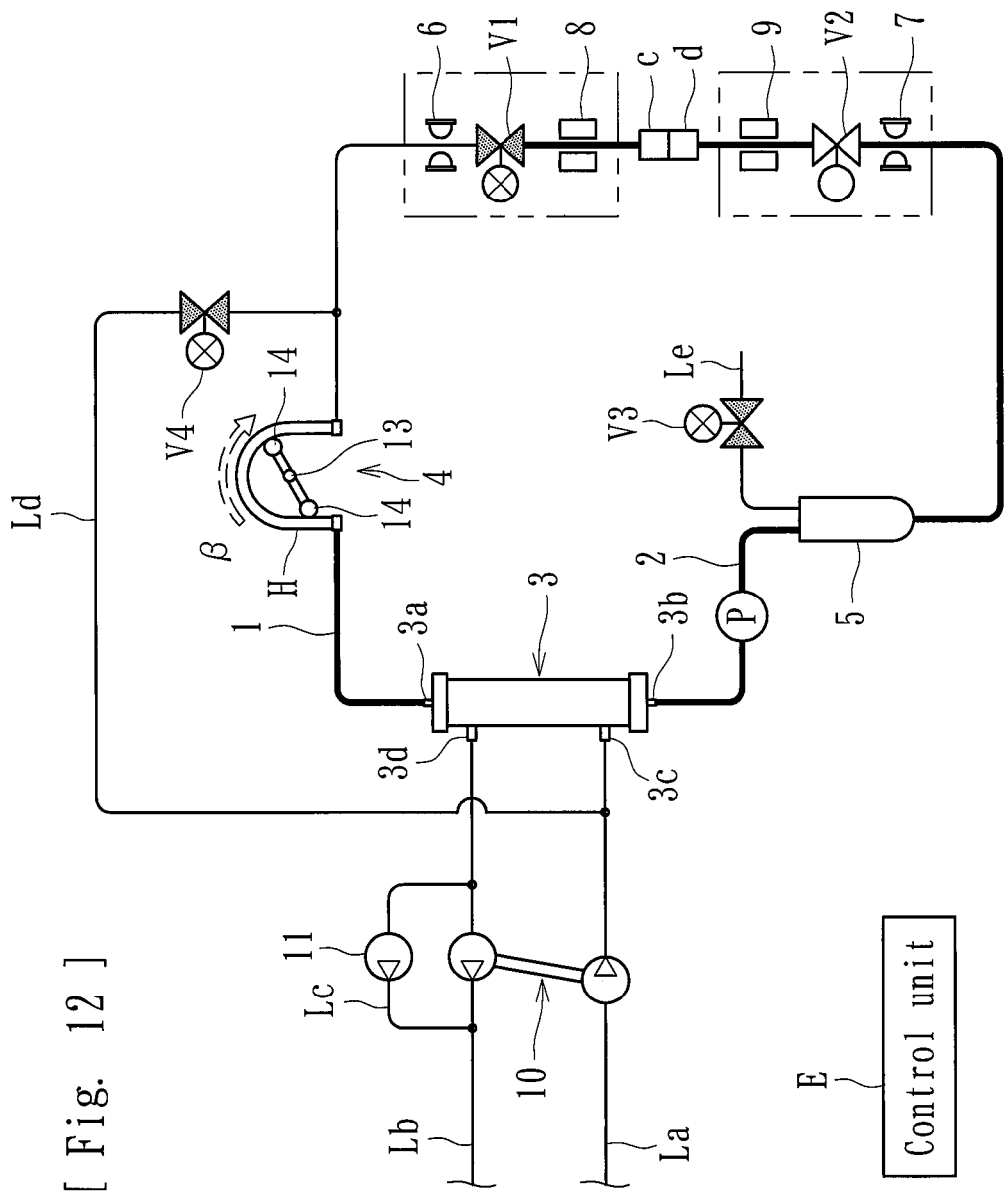
[Fig. 12]

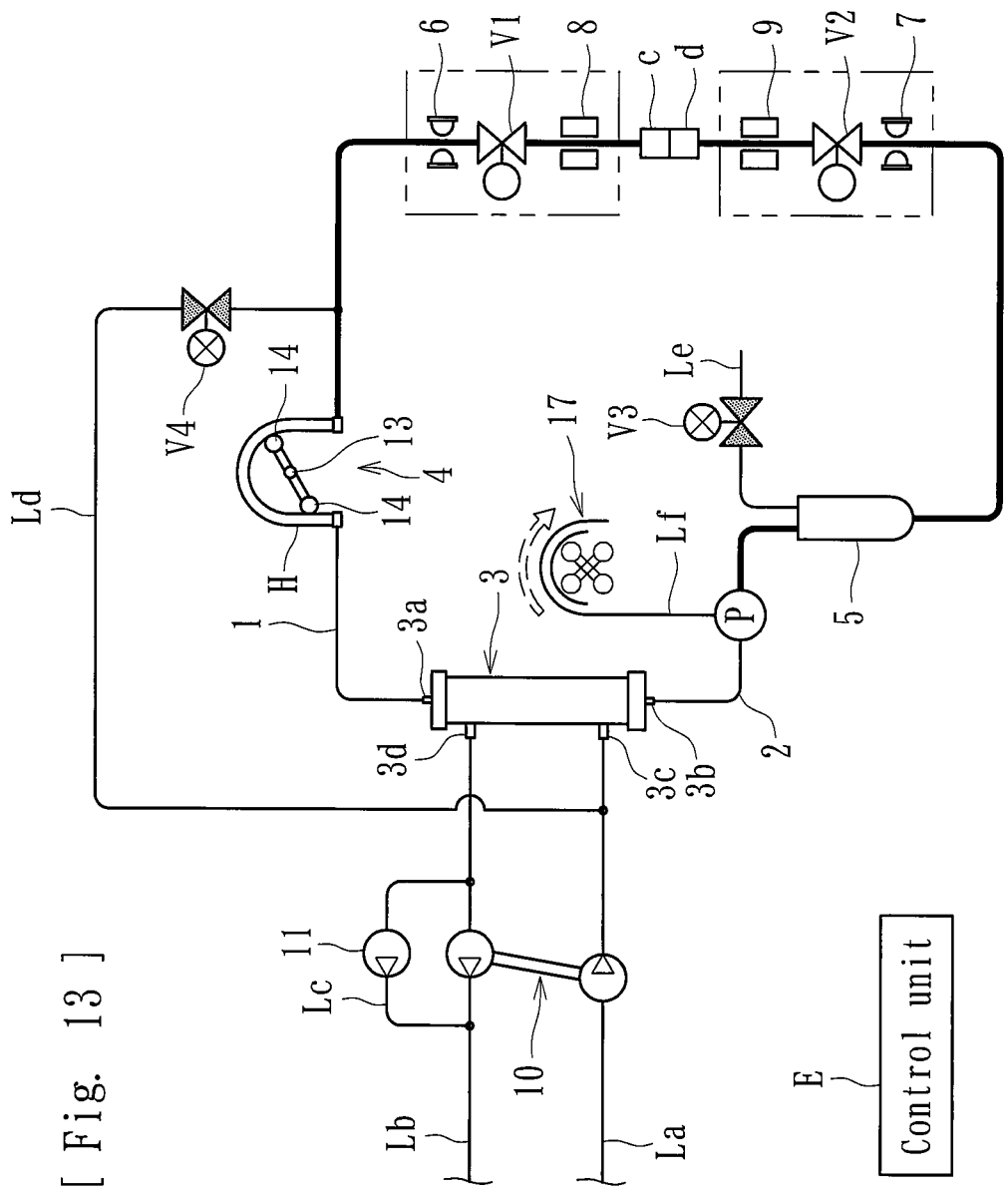
[Fig. 13]

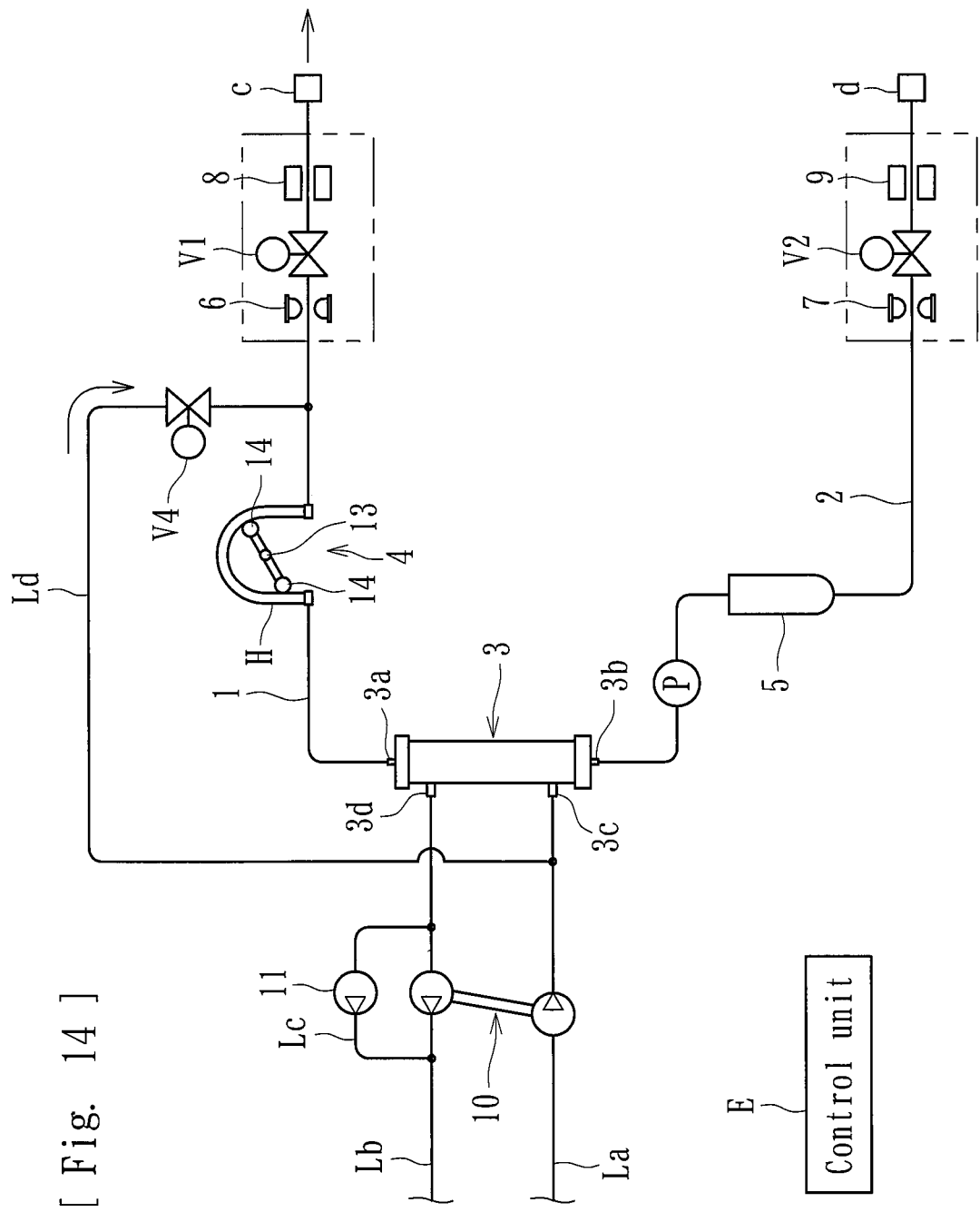
[Fig. 14]

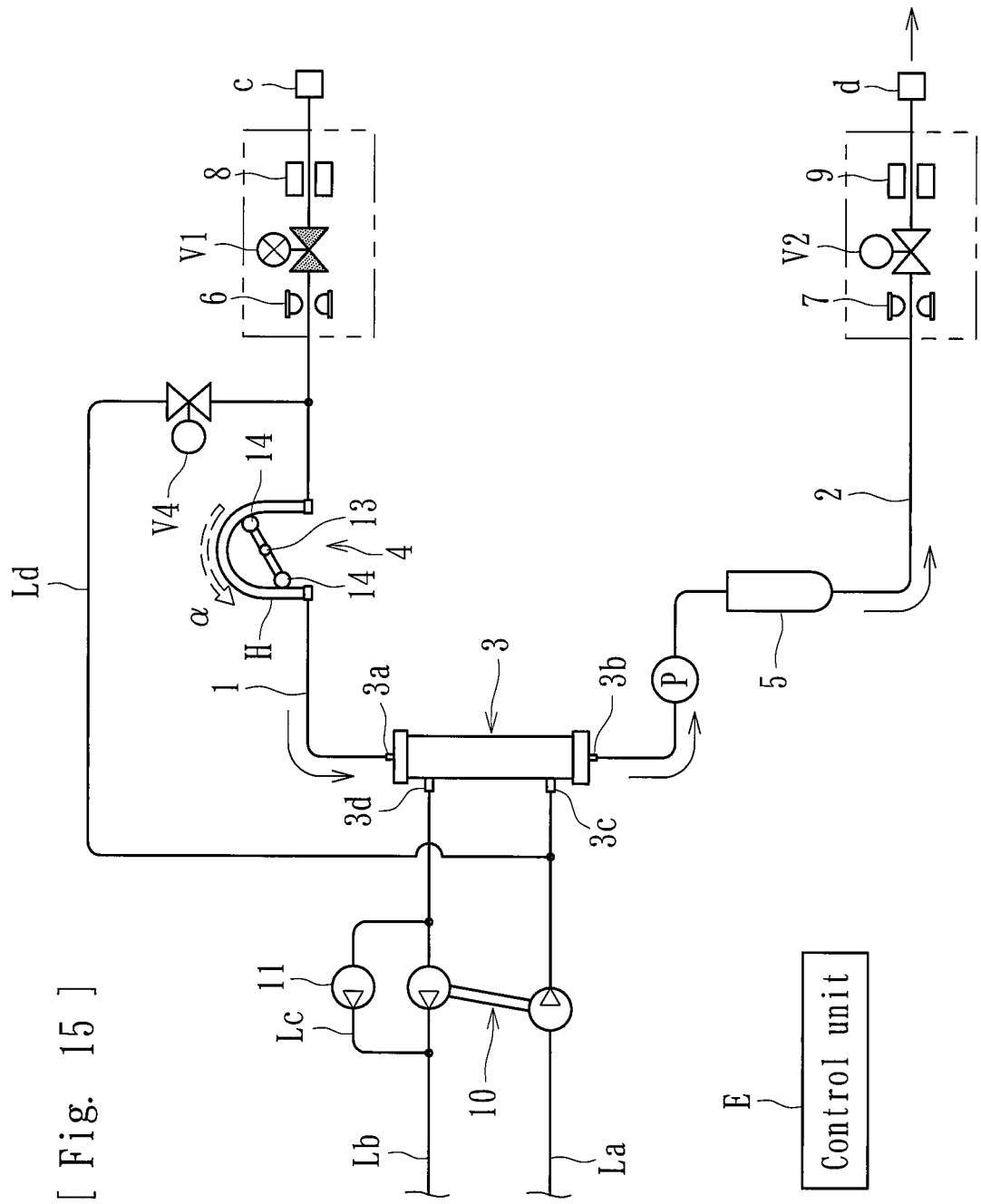
[Fig. 15]

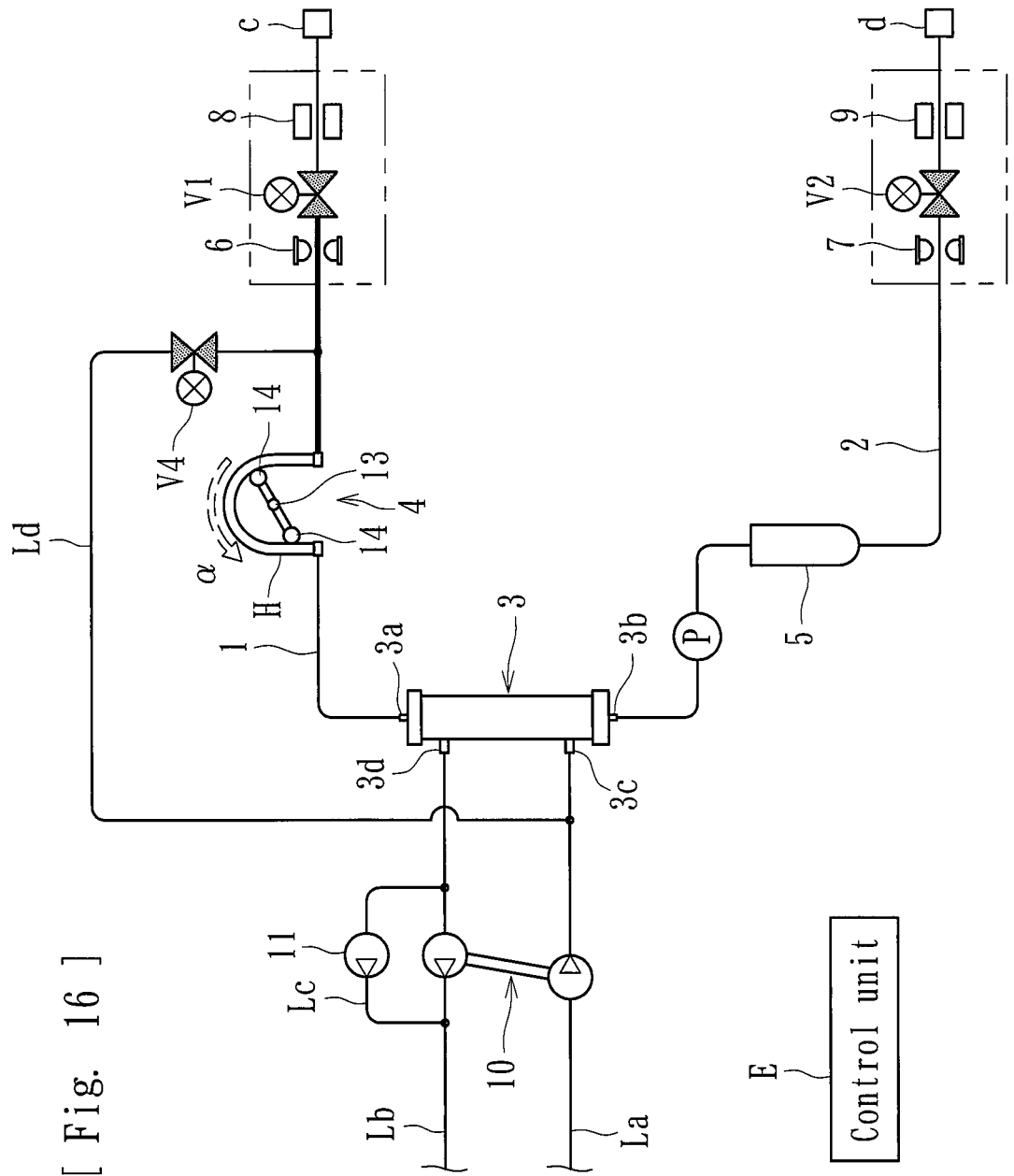
[Fig. 16]

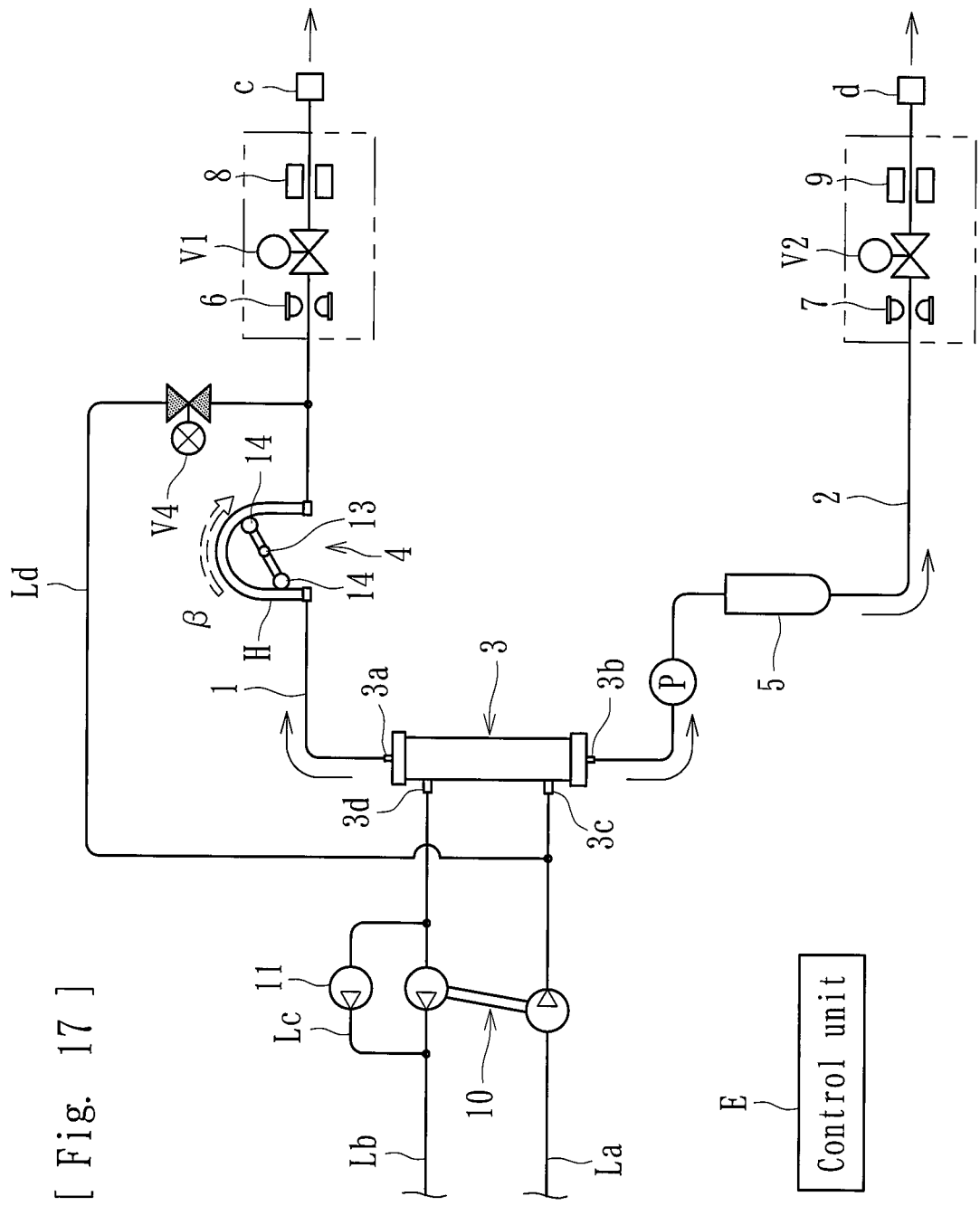
[Fig. 17]

[ Fig. 18 ]
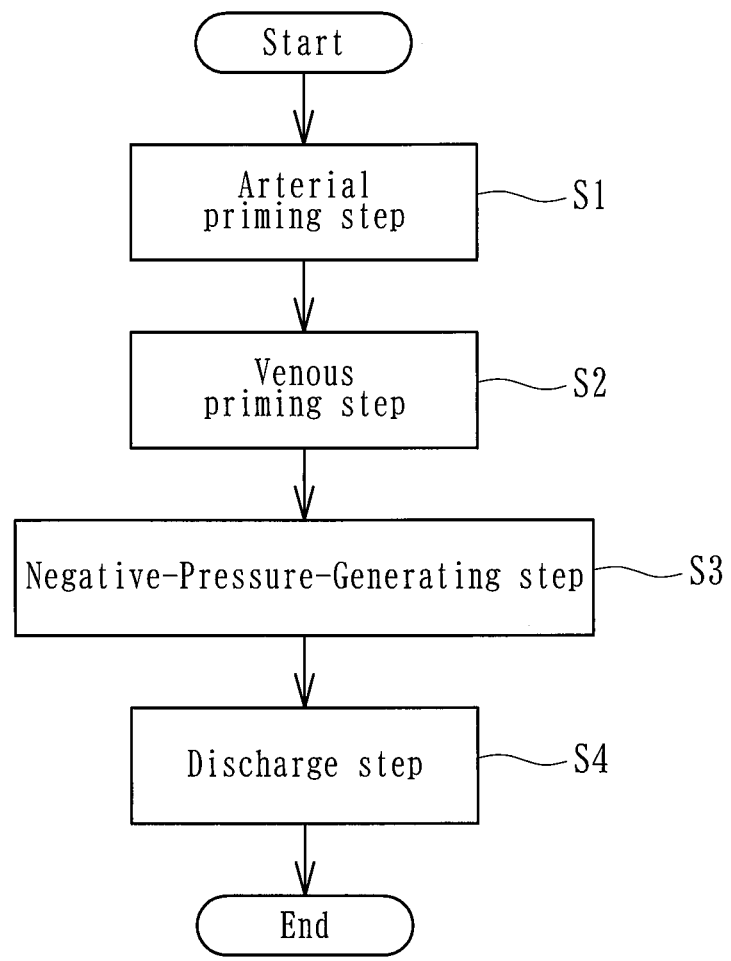

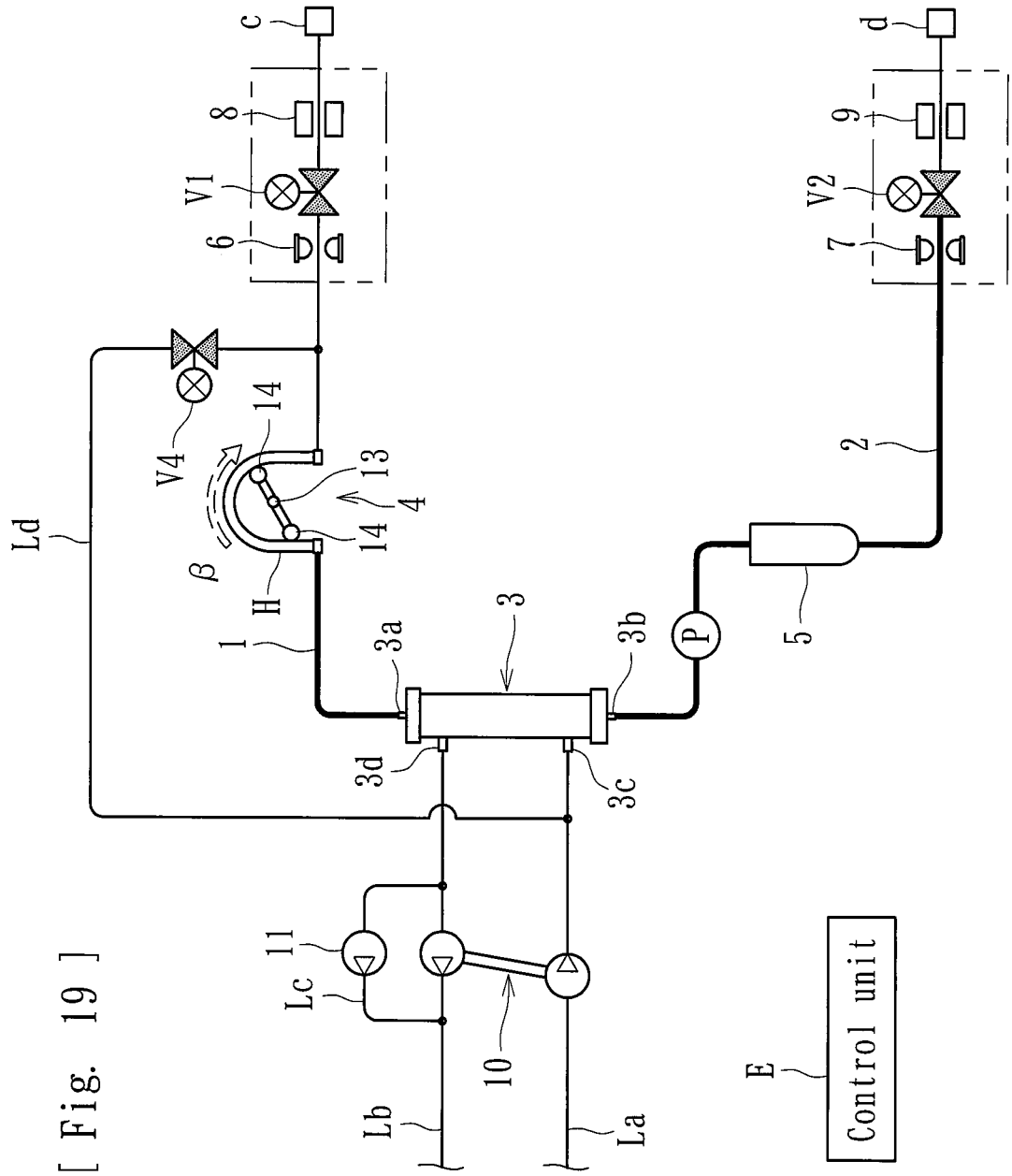
[Fig. 19]

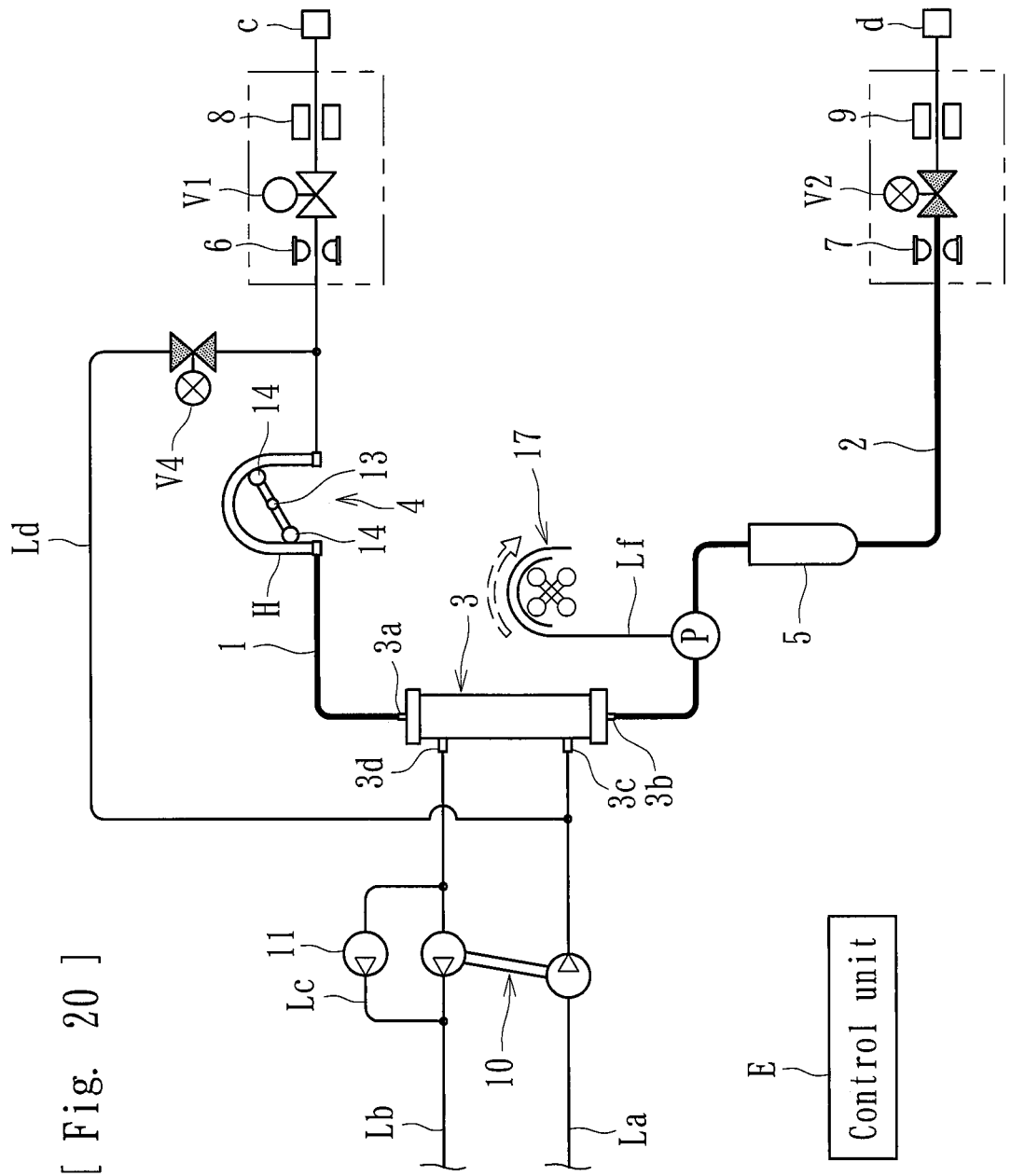
[Fig. 20]

EXTRACORPOREAL CIRCULATION APPARATUS AND METHOD OF DISCHARGING BUBBLES THEREFROM

CROSS-REFERENCE TO RELATED APPLICATION(S)

This application is a continuation of International Application No. PCT/JP2018/033151, filed on Sep. 7, 2018, which claims priority to Japanese Application No. 2017-172561, filed on Sep. 7, 2017, the entire disclosures of which are hereby incorporated by reference.

FIELD

The present invention relates to an extracorporeal circulation apparatus for purifying a patient's blood while causing the blood to extracorporeally circulate in dialysis treatment or the like performed with a dialyzer, and also relates to a method of discharging bubbles therefrom.

BACKGROUND

In general, dialysis treatment is performed by using a blood circuit for allowing blood collected from a patient to extracorporeally circulate and to be returned into the body. Such a blood circuit basically includes, for example, an arterial blood circuit and a venous blood circuit that are connected to a dialyzer (a blood purifier) including hollow fiber membranes. The arterial blood circuit and the venous blood circuit are provided at distal ends thereof with an arterial puncture needle and a venous puncture needle, respectively. Extracorporeal circulation of blood in the dialysis treatment is performed with the puncture needles puncturing the patient.

In particular, the arterial blood circuit is provided with a squeezable tube connected thereto and a peristaltic blood pump. The blood pump delivers liquid by squeezing the squeezable tube with a roller. When the blood pump is activated, the patient's blood can be caused to extracorporeally circulate through the blood circuit. Therefore, the blood in extracorporeal circulation undergoes blood purification treatment in the dialyzer.

Furthermore, the arterial blood circuit is provided with a priming-solution supply line connected thereto for supplying a priming solution to the blood circuit. Before the dialysis treatment, a priming process is performed in which a priming solution is supplied through a priming-solution supply line and is discharged through an overflow line, whereby bubbles in the blood circuit are discharged while flow routes in the blood circuit are filled with the priming solution (see PTL 1, for example).

PTL 1: Japanese Unexamined Patent Application Publication No. 2010-273693, the teachings of which are expressly incorporated by reference herein for all purposes.

SUMMARY

However, in the above known extracorporeal circulation apparatus, in particular, if microbubbles remain in the priming solution filled in the squeezable tube, a large volume of priming solution needs to be supplied at a high flow rate so as to discharge such microbubbles to the outside of the blood circuit. Moreover, such residual microbubbles may occur not only in the squeezable tube but also in all flow routes in the blood circuit that are to be filled with the priming solution. Hence, there has been an increasing demand for smooth and assured removal of residual microbubbles occurring in the priming process.

Accordingly, the present applicant has focused on a phenomenon in which generation of a negative pressure in any flow routes filled with the priming solution makes the residual microbubbles inflate and merge with adjoining bubbles into relatively large bubbles. Utilizing this phenomenon, the present applicant has examined the possibility of smoothly and assuredly discharging residual microbubbles from the squeezable tube.

The present invention has been conceived in view of the above circumstances and provides an extracorporeal circulation apparatus capable of smoothly and assuredly discharging residual microbubbles after the priming process, and a method of discharging bubbles therefrom.

According to the teachings herein, there is provided an extracorporeal circulation apparatus including a blood circuit including an arterial blood circuit and a venous blood circuit whose proximal ends are connected to a blood purifier, the blood circuit allowing a patient's blood to extracorporeally circulate from a distal end of the arterial blood circuit to a distal end of the venous blood circuit; a discharge unit through which a priming solution supplied into the blood circuit is discharged to an outside; a negative-pressure-generating unit that generates a negative pressure in a region of the blood circuit, the region being filled with the priming solution; and a control unit that controls the negative-pressure-generating unit. The control unit executes a priming step in which the priming solution supplied into the blood circuit is discharged through the discharge unit while a flow route in the blood circuit is filled with the priming solution; a negative-pressure-generating step in which, after the priming step, a negative pressure is generated in the region by the negative-pressure-generating unit; and a discharge step in which bubbles in the region subjected to the negative pressure generated in the negative-pressure-generating step are caused to flow and are discharged through the discharge unit.

According to the teachings herein, the extracorporeal circulation apparatus taught herein further includes a blood pump that delivers liquid by squeezing, with a roller, a squeezable tube connected to the arterial blood circuit. Furthermore, the region where a negative pressure is to be generated by the negative-pressure-generating unit includes at least part of the squeezable tube.

According to the teachings herein, in the extracorporeal circulation apparatus taught herein, the negative-pressure-generating unit includes the blood pump and a closing portion, the closing portion being configured to close the region of the blood circuit that is filled with the priming solution.

According to the teachings herein, the extracorporeal circulation apparatus taught herein further includes a level-adjusting pump connected to a predetermined position of the blood circuit and that adjusts a liquid surface at the predetermined position. Furthermore, the negative-pressure-generating unit includes the level-adjusting pump and a closing portion, the closing portion being configured to close the region of the blood circuit that is filled with the priming solution.

According to the teachings herein, in the extracorporeal circulation apparatus taught herein, the venous blood circuit is provided with an air-trap chamber connected thereto. Furthermore, the discharge unit is formed of an overflow line extending from a top of the air-trap chamber.

According to the teachings herein, in the extracorporeal circulation apparatus taught herein, the discharge unit is formed of the distal end of the arterial blood circuit or the distal end of the venous blood circuit.

According to the teachings herein, there is provided a method of discharging bubbles from an extracorporeal circulation apparatus. The apparatus includes a blood circuit including an arterial blood circuit and a venous blood circuit whose proximal ends are connected to a blood purifier, the blood circuit allowing a patient's blood to extracorporeally circulate from a distal end of the arterial blood circuit to a distal end of the venous blood circuit; a discharge unit through which a priming solution supplied into the blood circuit is discharged to an outside; and a negative-pressure-generating unit that generates a negative pressure in a region of the blood circuit, the region being filled with the priming solution. The method includes a priming step in which the priming solution supplied into the blood circuit is discharged through the discharge unit while a flow route in the blood circuit is filled with the priming solution; a negative-pressure-generating step in which, after the priming step, a negative pressure is generated in the region by the negative-pressure-generating unit; and a discharge step in which bubbles in the region subjected to the negative pressure generated in the negative-pressure-generating step are caused to flow and are discharged through the discharge unit.

According to the teachings herein, in the method of discharging bubbles from the extracorporeal circulation apparatus taught herein, the extracorporeal circulation apparatus further includes a blood pump that delivers liquid by squeezing, with a roller, a squeezable tube connected to the arterial blood circuit. Furthermore, the region where a negative pressure is to be generated by the negative-pressure-generating unit includes at least part of the squeezable tube.

According to the teachings herein, in the method of discharging bubbles from the extracorporeal circulation apparatus taught herein, the negative-pressure-generating unit includes the blood pump and a closing portion, the closing portion being configured to close the region of the blood circuit that is filled with the priming solution.

According to the teachings herein, in the method of discharging bubbles from the extracorporeal circulation apparatus taught herein, the extracorporeal circulation apparatus further includes a level-adjusting pump connected to a predetermined position of the blood circuit and that adjusts a liquid surface at the predetermined position. Furthermore, the negative-pressure-generating unit includes the level-adjusting pump and a closing portion, the closing portion being configured to close the region of the blood circuit that is filled with the priming solution.

According to the teachings herein, in the method of discharging bubbles from the extracorporeal circulation apparatus taught herein, the venous blood circuit is provided with an air-trap chamber connected thereto. Furthermore, the discharge unit is formed of an overflow line extending from a top of the air-trap chamber.

According to the teachings herein, in the method of discharging bubbles from the extracorporeal circulation apparatus taught herein, the discharge unit is formed of the distal end of the arterial blood circuit or the distal end of the venous blood circuit.

According to the teachings herein, the following are executed: the negative-pressure-generating step in which, after the priming step, a negative pressure is generated by the negative-pressure-generating unit in the region filled with the priming solution; and the discharge step in which bubbles in the region subjected to the negative pressure generated in the negative-pressure-generating step are caused to flow and are discharged through the discharge unit. Therefore, microbubbles remaining in the region filled with the priming solution can be made to inflate under the negative pressure generated in the negative-pressure-generating step and to merge into larger bubbles. Hence, the microbubbles remaining after the priming step can be discharged smoothly and assuredly.

According to the teachings herein, the extracorporeal circulation apparatus includes the blood pump that delivers liquid by squeezing, with the roller, the squeezable tube connected to the arterial blood circuit. Furthermore, the region where a negative pressure is to be generated by the negative-pressure-generating unit includes at least part of the squeezable tube. Therefore, after the priming step, microbubbles remaining in the squeezable tube can be discharged smoothly and assuredly.

According to the teachings herein, the negative-pressure-generating unit includes the blood pump and the closing portion, the closing portion being configured to close the region of the blood circuit that is filled with the priming solution. Therefore, the generation of a negative pressure in the region filled with the priming solution can be achieved with the use of the blood pump, which is necessary for blood purification treatment.

According to the teachings herein, the extracorporeal circulation apparatus includes the level-adjusting pump connected to the predetermined position of the blood circuit and that adjusts the liquid surface at the predetermined position. Furthermore, the negative-pressure-generating unit includes the level-adjusting pump and the closing portion, the closing portion being configured to close the region of the blood circuit that is filled with the priming solution. Therefore, the generation of a negative pressure in the region filled with the priming solution can be achieved with the use of the level-adjusting pump, which is necessary for adjusting the liquid surface.

According to the teachings herein, the venous blood circuit is provided with the air-trap chamber connected thereto. Furthermore, the discharge unit is formed of the overflow line extending from the top of the air-trap chamber. Therefore, when the priming step is executed with the distal end of the arterial blood circuit and the distal end of the venous blood circuit being connected to each other, microbubbles remaining in the region of the blood circuit that is filled with the priming solution can be discharged in a good manner through the overflow line.

According to the teachings herein, the discharge unit is formed of the distal end of the arterial blood circuit or the distal end of the venous blood circuit. Therefore, when the priming step is executed without connecting the distal end of the arterial blood circuit 1 and the distal end of the venous blood circuit 2 to each other, microbubbles remaining in the region of the blood circuit that is filled with the priming solution can be discharged in a good manner from the distal end of the arterial blood circuit or the distal end of the venous blood circuit.

BRIEF DESCRIPTION OF THE DRAWINGS

FIG. 1 is a schematic diagram of a dialysis apparatus (an extracorporeal circulation apparatus) according to a first embodiment of the present invention.

FIG. 2 is a perspective view of a blood pump applied to the dialysis apparatus.

FIG. 3 is a plan view of the blood pump with a squeezable tube attached thereto.

FIG. 4 includes schematic diagrams of a venous-pressure-measuring unit applied to the dialysis apparatus.

FIG. 5 is a schematic diagram of the dialysis apparatus executing a priming step (an overflow step).

FIG. 6 is a schematic diagram of the dialysis apparatus executing the priming step (a liquid-delivering step).

FIG. 7 is a schematic diagram of the dialysis apparatus executing a negative-pressure-generating step.

FIG. 8 is a schematic diagram of the dialysis apparatus executing a first discharge step.

FIG. 9 is a schematic diagram of the dialysis apparatus executing a second discharge step.

FIG. 10 is a flow chart illustrating a control process executed by a control unit of the dialysis apparatus.

FIG. 11 is a schematic diagram of a dialysis apparatus according to another embodiment of the present invention that is executing a negative-pressure-generating step.

FIG. 12 is a schematic diagram of a dialysis apparatus according to yet another embodiment of the present invention that is executing a negative-pressure-generating step.

FIG. 13 is a schematic diagram of a dialysis apparatus according to yet another embodiment of the present invention that is executing a negative-pressure-generating step.

FIG. 14 is a schematic diagram of a dialysis apparatus (an extracorporeal circulation apparatus) according to a second embodiment of the present invention that is executing a priming step (an arterial priming step).

FIG. 15 is a schematic diagram of the dialysis apparatus executing the priming step (a venous priming step).

FIG. 16 is a schematic diagram of the dialysis apparatus executing a negative-pressure-generating step.

FIG. 17 is a schematic diagram of the dialysis apparatus executing a discharge step.

FIG. 18 is a flow chart illustrating a control process executed by a control unit of the dialysis apparatus.

FIG. 19 is a schematic diagram of a dialysis apparatus according to another embodiment of the present invention that is executing a negative-pressure-generating step.

FIG. 20 is a schematic diagram of a dialysis apparatus according to yet another embodiment of the present invention that is executing a negative-pressure-generating step.

DETAILED DESCRIPTION

Embodiments of the present invention will now be described specifically with reference to the drawings.

An extracorporeal circulation apparatus according to a first embodiment is a dialysis apparatus intended for dialysis treatment and basically includes, as illustrated in FIG. 1, a blood circuit formed of an arterial blood circuit 1 and a venous blood circuit 2, a dialyzer 3 (a blood purifier) connected to a proximal end of the arterial blood circuit 1 and to a proximal end of the venous blood circuit 2 and that purifies blood flowing through the blood circuit, an air-trap chamber 5 connected to the venous blood circuit 2, a priming-solution supply line Ld connected to the arterial blood circuit 1 and through which a priming solution is supplied into the blood circuit, an overflow line Le (a discharge unit) through which the priming solution supplied into the blood circuit through the priming-solution supply line Ld is discharged to the outside, a negative-pressure-generating unit (in the present embodiment, a blood pump 4 and an electromagnetic valve V1 as a closing portion) that generates a negative pressure in a region of the blood circuit that is filled with the priming solution, and a control unit E that controls the negative-pressure-generating unit (the blood pump 4 and the electromagnetic valve V1).

The arterial blood circuit 1 is provided with an arterial puncture needle a connected to a distal end thereof through a connector c, and with the blood pump 4, which is of a peristaltic type, at a halfway position thereof. The venous blood circuit 2 is provided with a venous puncture needle b connected to a distal end thereof through a connector d, and with an air-trap chamber 5 connected to a halfway position thereof. Furthermore, the arterial blood circuit 1 and the venous blood circuit 2 are provided in respective distal portions thereof (near the respective connectors c and d) with respective electromagnetic valves V1 and V2 connected thereto, which close or open respective flow routes.

When the blood pump 4 is activated with the arterial puncture needle a and the venous puncture needle b puncturing the patient, the patient's blood flows through the arterial blood circuit 1 and reaches the dialyzer 3, where the blood is purified. Then, the blood flows through the venous blood circuit 2 while undergoing bubble removal in the air-trap chamber 5 and returns into the patient's body. That is, blood purification treatment is performed by purifying the patient's blood with the dialyzer 3 while causing the blood to extracorporeally circulate through the blood circuit from the distal end of the arterial blood circuit 1 to the distal end of the venous blood circuit 2. In this specification, the side of the puncture needle for blood removal (blood collection) is referred to as the "arterial" side, and the side of the puncture needle for blood return is referred to as the "venous" side. The "arterial" side and the "venous" side are not defined in accordance with which of the artery and the vein is to be the object of puncture.

The arterial blood circuit 1 is provided at a halfway position thereof (between the connection to the priming-solution supply line Ld and the dialyzer 3) with a squeezable tube H connected thereto, which is attachable to the blood pump 4 (specifically, to a fitting recess 12a provided in a stator 12 of the blood pump 4, which will be described in detail below with reference to FIGS. 2 and 3). The squeezable tube H is to be squeezed in the lengthwise direction while being compressed in the radial direction by rollers 14 (a squeezing unit) of the blood pump 4 (the peristaltic pump), whereby liquid in the squeezable tube H is caused to flow in the direction of rotation of a rotor 13. The squeezable tube H is a flexible tube that is softer and has a greater diameter than other flexible tubes forming the arterial blood circuit 1.

As illustrated in FIGS. 2 and 3, the blood pump 4 according to the present embodiment basically includes the stator 12, the rotor 13 that rotates on the inner side of the stator 12, the rollers 14 provided on the rotor 13, a pair of upper and lower guide pins 15, and holding portions 16 that hold and secure the squeezable tube H. In the drawings, a cover provided over the stator 12 of the blood pump 4 is not illustrated.

The stator 12 has the fitting recess 12a, into which the squeezable tube H is to be fitted. As illustrated in FIGS. 2 and 3, the squeezable tube H is fitted along the inner peripheral wall of the fitting recess 12a. The rotor 13, which is rotatably driven by a motor, is provided substantially in the center of the fitting recess 12a. The pair of (two) rollers 14 and the guide pins 15 are provided on a side face (a surface facing the inner peripheral wall of the fitting recess 12a) of the rotor 13.

The rollers 14 are rotatable on respective rotating shafts M (see FIG. 3) provided on the outer peripheral edge of the rotor 13. The rollers 14 compress the squeezable tube H, fitted in the fitting recess 12a, in the radial direction and squeeze the squeezable tube H in the lengthwise direction (the direction of blood flow) with the rotation of the rotor 13, whereby the blood is caused to flow through the arterial blood circuit 1. Specifically, when the rotor 13 is rotated with the squeezable tube H fitted in the fitting recess 12a, the squeezable tube H is compressed between each of the rollers 14 and the inner peripheral wall of the fitting recess 12a. With the rotation of the rotor 13, the squeezable tube H can be squeezed in the direction of rotation of the rotor 13 (in the lengthwise direction of the squeezable tube H). With such a squeezing motion, the blood in the arterial blood circuit 1 is delivered in the direction of rotation of the rotor 13. Thus, the blood can be caused to extracorporeally circulate through the arterial blood circuit 1.

In the blood pump 4 according to the present embodiment, when the rotor 13 is rotated normally and causes the rollers 14 to rotate in the same direction (a direction indicated by reference character α in FIG. 3) in such a manner as to move in the lengthwise direction of the squeezable tube H, the liquid can be delivered from the distal end of the arterial blood circuit 1 toward the dialyzer 3 (the blood purifier). When the rotor 13 is rotated reversely and causes the rollers 14 to rotate in the same direction (a direction indicated by reference character β in FIG. 3) in such a manner as to move in the lengthwise direction of the squeezable tube H, the liquid can be delivered from the dialyzer 3 (the blood purifier) toward the distal end of the arterial blood circuit 1.

As illustrated in FIG. 2, the guide pins 15 are a pair of upper and lower pin-like members projecting from the upper end and the lower end, respectively, of the rotor 13 toward the inner peripheral wall of the fitting recess 12a. The squeezable tube H is to be held between the pair of upper and lower guide pins 15. Specifically, while the rotor 13 is rotated, the pair of upper and lower guide pins 15 retain the squeezable tube H at a proper position and prevent the squeezable tube H from being displaced upward or downward from the fitting recess 12a.

The air-trap chamber 5 is provided with the overflow line Le (the discharge unit). The overflow line Le extends from the top of the air-trap chamber 5 with the distal end thereof being open to the atmosphere. The overflow line Le allows the liquid (the priming solution) overflowing from the air-trap chamber 5 to be discharged to the outside. The overflow line Le is provided with an electromagnetic valve V3, which is capable of closing or opening the flow route in the overflow line Le at an arbitrary timing.

The dialyzer 3 has, in a housing thereof, a blood inlet 3a (a blood introduction port), a blood outlet 3b (a blood delivery port), a dialysate inlet 3c (an inlet of a dialysate flow route, or a dialysate introduction port), and a dialysate outlet 3d (an outlet of the dialysate flow route, or a dialysate delivery port). The blood inlet 3a is connected to the proximal end of the arterial blood circuit 1. The blood outlet 3b is connected to the proximal end of the venous blood circuit 2. The dialysate inlet 3c and the dialysate outlet 3d are connected to a dialysate introduction line La and a dialysate drain line Lb, respectively, extending from a dialysis-apparatus body.

The dialyzer 3 houses a plurality of hollow fibers (not illustrated). The hollow fibers form blood purification membranes for purifying the blood. The blood purification membranes in the dialyzer 3 define blood flow routes (each extending between the blood inlet 3a and the blood outlet 3b) through which the patient's blood flows and dialysate flow routes (each extending between the dialysate inlet 3c and the dialysate outlet 3d) through which dialysate flows. The hollow fibers forming the blood purification membranes each have a number of very small holes (pores) extending therethrough from the outer peripheral surface to the inner peripheral surface, thereby forming a hollow fiber membrane. Impurities and the like contained in the blood permeate through the follow fiber membranes into the dialysate.

A duplex pump 10 is provided over the dialysate introduction line La and the dialysate drain line Lb in the dialysis-apparatus body. The dialysate drain line Lb is provided with a bypass line Lc that bypasses the duplex pump 10. The bypass line Lc is provided with an ultrafiltration pump 11 for removing water from the patient's blood flowing through the dialyzer 3. One end of the dialysate introduction line La is connected to the dialyzer 3 (the dialysate inlet 3c), and the other end is connected to a dialysate supply device (not illustrated) that prepares a dialysate at a predetermined concentration. One end of the dialysate drain line Lb is connected to the dialyzer 3 (the dialysate outlet 3d), and the other end is connected to a drainage unit, not illustrated. The dialysate supplied from the dialysate supply device flows through the dialysate introduction line La into the dialyzer 3, and further flows through the dialysate drain line Lb into the drainage unit.

One end of the priming-solution supply line Ld is connected to a predetermined position of the dialysate introduction line La between the duplex pump 10 and the dialyzer 3, and the other end is connected to a predetermined position of the arterial blood circuit 1 between the blood pump 4 and an arterial bubble-detecting unit 6. The priming-solution supply line Ld is provided with an electromagnetic valve V4 that closes or opens a corresponding flow route at an arbitrary timing. When the electromagnetic valve V4 is opened, the dialysate (the priming solution) in the dialysate introduction line La is supplied to the arterial blood circuit 1.

The arterial blood circuit 1 is provided on the distal portion thereof with the arterial bubble-detecting unit 6, which detects bubbles in the liquid flowing through a corresponding position. The venous blood circuit 2 is provided on the distal portion thereof with a venous bubble-detecting unit 7, which detects bubbles in the liquid flowing through a corresponding position. Reference numerals 8 and 9 in the drawing denote blood identifiers provided on the respective distal portions of the arterial blood circuit 1 and the venous blood circuit 2.

Furthermore, the venous blood circuit 2 according to the present embodiment is provided with a venous-pressure-measuring unit P that measures venous pressure. The venous-pressure-measuring unit P is provided at a position of the venous blood circuit 2 between the dialyzer 3 and the air-trap chamber 5 and measures the hydraulic pressure of the blood flowing through the venous blood circuit 2, thereby measuring the venous pressure of the patient during the blood purification treatment in a time-course manner.

The venous-pressure-measuring unit P according to the present embodiment includes, for example, a chamber portion connected to the venous blood circuit 2, and a sensor or the like that measures the hydraulic pressure in the chamber portion. The chamber portion is filled with the priming solution before the blood purification treatment and with the blood during the blood purification treatment. That is, no air layer is formed in the chamber portion. Thus, the hydraulic pressure of the liquid (blood) flowing through the venous-pressure-measuring unit P is directly measured with the sensor, and the venous pressure of the patient during the blood purification treatment is monitored in a time-course manner.

Specifically, as illustrated in FIG. 4(a), the venous-pressure-measuring unit P according to the present embodiment includes a chamber portion m1 connected to the venous blood circuit 2, and a membrane m2 provided in the chamber portion m1 and that does not allow liquid to permeate therethrough. In the chamber portion m1, a liquid-phase part Q1 filled with liquid and a gas-phase part Q2 filled with air can be formed. The gas-phase part Q2 is provided with an atmosphere release line Lf, to which a level-adjusting pump 17 formed of a peristaltic pump is attached. As illustrated in part (b) of the drawing, when the level-adjusting pump 17 is activated, air in the gas-phase part Q2 is discharged to the outside, whereby the position of the membrane m2 (the liquid surface) in the chamber portion m1 is adjusted (in the present embodiment, air in the chamber portion m1 is all discharged, so that no air layer is formed).

The electromagnetic valves V1 to V4, each making the above opening and closing motion, open and close the respective flow routes at the respective positions. The opening and closing motion is controlled by the control unit E, which is a microcomputer or the like. In particular, the control unit E according to the present embodiment receives a detection signal generated by the venous bubble-detecting unit 7 and controls the blood pump 4 and the electromagnetic valves V1 to V4, to all of which the control unit E is electrically connected.

The control unit E according to the present embodiment sequentially executes a priming step in which, before the dialysis treatment (before the blood purification treatment), the priming solution supplied through the priming-solution supply line Ld is discharged through the overflow line Le (the discharge unit) while flow routes in the blood circuit are filled with the priming solution; a negative-pressure-generating step in which, after the priming step, a negative pressure is generated by the blood pump 4 and the electromagnetic valve V1 (the negative-pressure-generating unit) in the region filled with the priming solution; and a discharge step in which bubbles in the region subjected to the negative pressure generated in the negative-pressure-generating step are caused to flow and are discharged through the overflow line Le (the discharge unit).

Now, a control process executed by the control unit E according to the present embodiment will be described with reference to the flow chart illustrated in FIG. 10.

Before the blood purification treatment, as illustrated in FIGS. 5 and 6, the dialyzer 3 is set with the blood inlet 3a thereof being oriented upward (and is fixed with a fixing member, not illustrated). Furthermore, the connector c and the connector d are connected to each other, whereby the respective flow routes are made to communicate with each other. Then, the priming step (including an overflow step S1 and a liquid-delivering step S2) is executed. In the priming step, the priming solution supplied through the priming-solution supply line Ld is discharged through the overflow line Le (the discharge unit) while flow routes in the blood circuit are filled with the priming solution. In the present embodiment, the overflow step S1 (FIG. 5) and the liquid-delivering step S2 (FIG. 6) are executed repeatedly.

In the overflow step S1, as illustrated in FIG. 5, the blood pump 4 is stopped with the electromagnetic valves (V1 to V4) being open, whereby the priming solution (the dialysate) supplied through the priming-solution supply line Ld is caused to flow into the air-trap chamber 5, and the priming solution overflowing from the air-trap chamber 5 is discharged to the outside through the overflow line Le. Thus, the priming solution (the dialysate) supplied through the priming-solution supply line Ld fills a flow route extending from the connection between the arterial blood circuit 1 and the priming-solution supply line Ld through the connection between the distal end of the arterial blood circuit 1 and the distal end of the venous blood circuit 2 to the air-trap chamber 5, and also fills the air-trap chamber 5.

When a predetermined time elapses after the overflow step S1 is started, the liquid-delivering step S2 is executed. In the liquid-delivering step S2, as illustrated in FIG. 6, the blood pump 4 is rotated reversely (rotated in the direction β indicated in FIG. 6) with the electromagnetic valves (V1 and V2) being open and the electromagnetic valves (V3 and V4) being closed, whereby the priming solution (the dialysate) supplied in the overflow step S1 is delivered (caused to circulate) through the blood circuit. Thus, the priming solution flows through the blood-side flow routes in the dialyzer 3 from the lower side toward the upper side. Therefore, bubbles smoothly move upward and are removed.

After the above liquid-delivering step S2, whether any bubbles have been detected by the venous bubble-detecting unit 7 is checked (S3). If it is judged that bubbles have been detected, the overflow step S1 is executed again. After the overflow step S1 is continued for a predetermined time, the liquid-delivering step S2 is executed. Then, whether any bubbles have been detected is checked again in S3. As the overflow step S1 and the liquid-delivering step S2 are repeatedly executed until no bubbles are detected by the venous bubble-detecting unit 7, the blood circuit and the air-trap chamber 5 become fully filled with the priming solution.

If it is judged that no bubbles are detected by the venous bubble-detecting unit 7 in S3 and the priming step (including the overflow step S1 and the liquid-delivering step S2) is thus ended, the flow routes in the arterial blood circuit 1 and in the venous blood circuit 2 and the blood flow routes in the dialyzer 3 become fully filled with the priming solution (a filled state), and the air-trap chamber 5 and the chamber portion of the venous-pressure-measuring unit P also become fully filled with the priming solution (a state where no air layer is formed).

When the priming step is ended as above, the negative-pressure-generating step S4 is executed. In the negative-pressure-generating step S4, as illustrated in FIG. 7, the blood pump 4 is rotated normally (rotated in the direction α indicated in FIG. 7) with the electromagnetic valves (V1, V3, and V4) being closed and the electromagnetic valve V2 being open, whereby a negative pressure is generated in the region filled with the priming solution. In this case, the negative-pressure-generating unit is formed of the blood pump 4 and the electromagnetic valve V1 (the closing portion).

Specifically, when the blood pump 4 is rotated normally (rotated in the direction α indicated in FIG. 7) with the electromagnetic valves (V1 and V4) being closed, a negative pressure can be generated not only in a flow route in the arterial blood circuit 1 between the blood pump 4 and the electromagnetic valve V1 but also in a region (an arbitrary region) including part of the squeezable tube H (a flow route before the region that is being squeezed by the rollers 14). Therefore, microbubbles remaining in the above region (particularly in the part of the squeezable tube H) can be made to inflate and merge with adjoining bubbles into relatively larger bubbles. Thus, with the negative pressure generated in the negative-pressure-generating step S4, the residual microbubbles can be made larger, and such bubbles can be relatively easily caused to flow at the flow rate driven by the blood pump 4.

Subsequently, the discharge step (including a first discharge step S5 and a second discharge step S6) is executed sequentially in which the bubbles in the region subjected to the negative pressure generated in the negative-pressure-generating step S4 are caused to flow and are discharged through the overflow line Le (the discharge unit). In the first discharge step S5, as illustrated in FIG. 8, the blood pump 4 is rotated reversely with the electromagnetic valves (V1 and V2) being open and the electromagnetic valves (V3 and V4) being closed, whereby the bubbles having grown larger under the negative pressure generated in the negative-pressure-generating step S4 (the bubbles inflated under the negative pressure and merged into larger bubbles) are caused to flow into the air-trap chamber 5.

After the first discharge step S5, the second discharge step S6 is executed. In the second discharge step S6, as illustrated in FIG. 9, the blood pump 4 is stopped with the electromagnetic valves (V1 to V4) being open, whereby the bubbles having flowed into the air-trap chamber 5 in the first discharge step S5 can be discharged to the outside through the overflow line Le. Thus, through the first discharge step S5 and the second discharge step S6, the bubbles having grown larger under the negative pressure generated in the negative-pressure-generating step S4 (the bubbles inflated under the negative pressure and merged into larger bubbles) can be discharged to the outside.

According to the present embodiment, after the priming step (including the overflow step S1 and the liquid-delivering step S2), the following are executed: the negative-pressure-generating step S4 in which a negative pressure is generated by the blood pump 4 and the electromagnetic valve V1 (the negative-pressure-generating unit) in the region filled with the priming solution, and the discharge step (including the first discharge step S5 and the second discharge step S6) in which bubbles in the region subjected to the negative pressure generated in the negative-pressure-generating step S4 are caused to flow and are discharged through the overflow line Le (the discharge unit). Therefore, microbubbles remaining in the region filled with the priming solution can be made to inflate under the negative pressure generated in the negative-pressure-generating step S4 and to merge into larger bubbles. Hence, the microbubbles remaining after the priming step can be discharged smoothly and assuredly.

According to the present embodiment, the extracorporeal circulation apparatus includes the blood pump 4 that delivers liquid by squeezing, with the rollers 14, the squeezable tube H connected to the arterial blood circuit 1. Furthermore, the region where a negative pressure is to be generated by the negative-pressure-generating unit (in the present embodiment, the blood pump 4 and the electromagnetic valve V1) includes at least part of the squeezable tube H. Therefore, after the priming step, microbubbles remaining in the squeezable tube H can be discharged smoothly and assuredly. In particular, the negative-pressure-generating unit according to the present embodiment includes the blood pump 4 and the electromagnetic valve V1 (the closing portion), the electromagnetic valve V1 being configured to close the region of the blood circuit that is filled with the priming solution. Therefore, the generation of a negative pressure in the region filled with the priming solution can be achieved with the use of the blood pump 4, which is necessary for blood purification treatment.

According to the present embodiment, the venous blood circuit 2 is provided with the air-trap chamber 5 connected thereto. Furthermore, the discharge unit for discharging bubbles is formed of the overflow line Le extending from the top of the air-trap chamber 5. Therefore, when the priming step is executed with the distal end of the arterial blood circuit 1 and the distal end of the venous blood circuit 2 being connected to each other, microbubbles remaining in the region of the blood circuit that is filled with the priming solution can be discharged in a good manner through the overflow line Le.

In the negative-pressure-generating step S4 according to the present embodiment, as illustrated in FIG. 7, the blood pump 4 is rotated normally (rotated in the direction α indicated in FIG. 7) with the electromagnetic valves (V1, V3, and V4) being closed and the electromagnetic valve V2 being open. Alternatively, as illustrated in FIG. 11, the blood pump 4 may be rotated normally (rotated in the direction α indicated in FIG. 11) with the electromagnetic valves (V2, V3, and V4) being closed and the electromagnetic valve V1 being open, whereby a negative pressure may be generated in the flow routes in the region represented by a bold line in the drawing. In this case, the negative-pressure-generating unit is formed of the blood pump 4 and the electromagnetic valve V2 (the closing portion).

As another alternative, as illustrated in FIG. 12, the blood pump 4 may be rotated reversely with the electromagnetic valves (V1, V3, and V4) being closed and the electromagnetic valve V2 being open, whereby a negative pressure may be generated in the flow routes in the region represented by a bold line in the drawing. In such a case, the negative-pressure-generating unit is formed of the blood pump 4 and the electromagnetic valve V1 (the closing portion). In such a case as well, the region where a negative pressure is to be generated by the negative-pressure-generating unit includes at least part of the squeezable tube H. Therefore, after the priming step, microbubbles remaining in the squeezable tube H can be discharged smoothly and assuredly. Furthermore, in such a case, microbubbles adhered to the blood inlet 3a of the dialyzer 3 also inflate under the negative pressure generated by the negative-pressure-generating unit and merge together to form larger bubbles. Such bubbles can therefore be discharged easily.

As illustrated in FIG. 13, the extracorporeal circulation apparatus may include the level-adjusting pump 17 (see FIGS. 13 and 4) connected to the venous-pressure-measuring unit P at a predetermined position of the blood circuit (the venous blood circuit 2) and that adjusts the liquid surface at the predetermined position. Furthermore, the negative-pressure-generating unit may be formed of the level-adjusting pump 17, and the rollers 14, serving as the closing portion, of the blood pump 4. As illustrated in the drawings, the level-adjusting pump 17 is attached to the atmosphere release line Lf extending from the venous-pressure-measuring unit P. The level-adjusting pump 17 adjusts the liquid surface by discharging air from the air layer formed in the venous-pressure-measuring unit P to the outside through the atmosphere release line Lf (in the present embodiment, air in the chamber portion of the venous-pressure-measuring unit P is all discharged so that no air layer is formed).

Thus, in the negative-pressure-generating step S4, as illustrated in FIG. 13, while the blood pump 4 is stopped, the level-adjusting pump 17 is activated with the electromagnetic valves (V3 and V4) being closed and the electromagnetic valves (V1 and V2) being open, whereby a negative pressure can be generated in the region filled with the priming solution (the region represented by a bold line in the drawing). In this case, the closing portion of the negative-pressure-generating unit is formed of the rollers 14 of the blood pump 4 in the stopped state.

To summarize, if the extracorporeal circulation apparatus includes the level-adjusting pump 17 and if the negative-pressure-generating unit includes the level-adjusting pump 17 and the closing portion (the rollers 14 of the blood pump 4) with which the region of the blood circuit that is filled with the priming solution is closed, the generation of a negative pressure in the region filled with the priming solution can be achieved with the use of the level-adjusting pump 17, which is necessary for adjusting the liquid surface.

Now, a second embodiment of the present invention will be described.

As with the case of the first embodiment, an extracorporeal circulation apparatus according to the present embodiment is a dialysis apparatus intended for dialysis treatment and basically includes, as illustrated in FIG. 14, a blood circuit formed of an arterial blood circuit 1 and a venous blood circuit 2, a dialyzer 3 (a blood purifier) connected to a proximal end of the arterial blood circuit 1 and to a proximal end of the venous blood circuit 2 and that purifies blood flowing through the blood circuit, an air-trap chamber 5 connected to the venous blood circuit 2, a priming-solution supply line Ld connected to the arterial blood circuit 1 and through which a priming solution is supplied into the blood circuit, a negative-pressure-generating unit (in the present embodiment, a blood pump 4 and an electromagnetic valve V1 as a closing portion) that generates a negative pressure in a region of the blood circuit that is filled with the priming solution, and a control unit E that controls the negative-pressure-generating unit (the blood pump 4 and the electromagnetic valve V1).

The discharge unit (the discharge unit that allows the priming solution supplied into the blood circuit through the priming-solution supply line Ld to be discharged to the outside) according to the present embodiment is formed of a distal end of the arterial blood circuit 1 or a distal end of the venous blood circuit 2. The present embodiment does not employ the overflow line Le, which extends from the air-trap chamber 5 according to the first embodiment. Elements that are the same as those described in the first embodiment are denoted by corresponding ones of the reference numerals, and detailed description of those elements is omitted.

Now, a control process executed by the control unit E according to the present embodiment will be described with reference to the flow chart illustrated in FIG. 18.

Before the blood purification treatment, as illustrated in FIGS. 14 and 15, the dialyzer 3 is set with the blood inlet 3a thereof being oriented upward (and is fixed with a fixing member, not illustrated). Furthermore, the connector c and the connector d are each freed (the connectors are not connected to each other). Then, the priming step (including an arterial priming step S1 and a venous priming step S2) is executed. In the priming step, the priming solution supplied through the priming-solution supply line Ld is discharged from the distal ends (the discharge unit) of the arterial blood circuit 1 and the venous blood circuit 2 while flow routes in the blood circuit are filled with the priming solution. In the present embodiment, the arterial priming step S1 (FIG. 14) and the venous priming step S2 (FIG. 15) are executed.

In the arterial priming step S1, as illustrated in FIG. 14, the blood pump 4 is stopped with the electromagnetic valves (V1, V2, and V4) being open, whereby the priming solution (the dialysate) supplied through the priming-solution supply line Ld is caused to flow to the distal end of the arterial blood circuit 1 and is discharged from the distal end to the outside. Thus, the priming solution (the dialysate) supplied through the priming-solution supply line Ld fills a flow route extending from the connection between the arterial blood circuit 1 and the priming-solution supply line Ld to the distal end of the arterial blood circuit 1.

When a predetermined time elapses after the arterial priming step S1 is started, the venous priming step S2 is executed. In the venous priming step S2, as illustrated in FIG. 15, the blood pump 4 is rotated normally with the electromagnetic valves (V2 and V4) being open and the electromagnetic valve V1 being closed, whereby the priming solution (the dialysate) supplied through the priming-solution supply line Ld is caused to flow to the distal end of the venous blood circuit 2 and is discharged from the distal end to the outside. Thus, the priming solution (the dialysate) supplied through the priming-solution supply line Ld fills a flow route extending from the connection between the arterial blood circuit 1 and the priming-solution supply line Ld through the blood flow routes in the dialyzer 3 to the distal end of the venous blood circuit 2.

Subsequently, when a predetermined time elapses after the venous priming step S2 is started and the priming step is thus ended, the flow routes in the arterial blood circuit 1 and in the venous blood circuit 2 and the blood flow routes in the dialyzer 3 become fully filled with the priming solution (a filled state), and the air-trap chamber 5 and the chamber portion of the venous-pressure-measuring unit P also become fully filled with the priming solution (a state where no air layer is formed).

When the priming step is ended as above, the negative-pressure-generating step S3 is executed. In the negative-pressure-generating step S3, as illustrated in FIG. 16, the blood pump 4 is rotated normally with the electromagnetic valves (V1, V2, and V4) being closed, whereby a negative pressure is generated in the region filled with the priming solution. In this case, the negative-pressure-generating unit is formed of the blood pump 4 and the electromagnetic valve V1 (the closing portion).

Specifically, when the blood pump 4 is rotated normally with the electromagnetic valves (V1, V2, and V4) being closed, a negative pressure can be generated in the flow route in the arterial blood circuit 1 between the blood pump 4 and the electromagnetic valve V1 and in a region (an arbitrary region) including part of the squeezable tube H (a flow route before the region that is being squeezed by the rollers 14). Therefore, microbubbles remaining in the above region (particularly in the part of the squeezable tube H) can be made to inflate and merge with adjoining bubbles into relatively larger bubbles. Thus, with the negative pressure generated in the negative-pressure-generating step S3, the residual microbubbles can be made larger, and such bubbles can be relatively easily caused to flow at the flow rate at which the blood pump 4 is driven.

Subsequently, the discharge step S4 is executed in which the bubbles in the region subjected to the negative pressure generated in the negative-pressure-generating step S3 are caused to flow and are discharged from the distal end (the discharge unit) of the arterial blood circuit 1. In the discharge step S4, as illustrated in FIG. 17, the blood pump 4 is rotated reversely with the electromagnetic valves (V1 and V2) being open and the electromagnetic valve V4 being closed, whereby the bubbles having grown larger under the negative pressure generated in the negative-pressure-generating step S3 are discharged from the distal end of the arterial blood circuit 1.

Thus, through the discharge step S4, the bubbles having grown larger under the negative pressure generated in the negative-pressure-generating step S3 (the bubbles inflated under the negative pressure and merged into larger bubbles) can be discharged to the outside. In the discharge step S4 according to the present embodiment, the dialysate is back-filtered from the dialysate flow routes to the blood flow routes in the dialyzer 3, and therefore flows not only toward the arterial blood circuit 1 but also toward the venous blood circuit 2 to be discharged from the respective distal ends.

According to the present embodiment, after the priming step (including the arterial priming step S1 and the venous priming step S2), the following are executed: the negative-pressure-generating step S3 in which a negative pressure is generated by the blood pump 4 and the electromagnetic valve V1 (the negative-pressure-generating unit) in the region filled with the priming solution, and the discharge step in which bubbles in the region subjected to the negative pressure generated in the negative-pressure-generating step S3 are caused to flow and are discharged from the distal end (the discharge unit) of the arterial blood circuit 1. Therefore, microbubbles remaining in the region filled with the priming solution can be made to inflate under the negative pressure generated in the negative-pressure-generating step S3 and to merge into larger bubbles. Hence, microbubbles remaining after the priming step can be discharged smoothly and assuredly.

According to the present embodiment, the extracorporeal circulation apparatus includes the blood pump 4 that delivers liquid by squeezing, with the rollers 14, the squeezable tube H connected to the arterial blood circuit 1. Furthermore, the region where a negative pressure is to be generated by the negative-pressure-generating unit (in the present embodiment, the blood pump 4) includes at least part of the squeezable tube H. Therefore, after the priming step, microbubbles remaining in the squeezable tube H can be discharged smoothly and assuredly. In particular, the negative-pressure-generating unit according to the present embodiment includes the blood pump 4 and the electromagnetic valve V1 (the closing portion), the electromagnetic valve V1 being configured to close the region of the blood circuit that is filled with the priming solution. Therefore, the generation of a negative pressure in the region filled with the priming solution can be achieved with the use of the blood pump 4, which is necessary for blood purification treatment.

According to the present embodiment, the discharge unit for discharging bubbles is formed of the distal end of the arterial blood circuit 1 (or may be the distal end of the venous blood circuit 2). Therefore, when the priming step is executed without connecting the distal end of the arterial blood circuit 1 and the distal end of the venous blood circuit 2 to each other, microbubbles remaining in the region of the blood circuit that is filled with the priming solution can be discharged in a good manner from the distal end of the arterial blood circuit 1 (or the distal end of the venous blood circuit).

In the negative-pressure-generating step S3 according to the present embodiment, as illustrated in FIG. 16, the blood pump 4 is rotated normally with the electromagnetic valves (V1, V2, and V4) being closed. Alternatively, as illustrated in FIG. 19, the blood pump 4 may be rotated reversely with the electromagnetic valves (V1, V2, and V4) being closed, whereby a negative pressure may be generated in the flow routes in the region represented by a bold line in the drawing. In such a case, the negative-pressure-generating unit is formed of the blood pump 4, and the electromagnetic valve V1 and the electromagnetic valve V2 (the closing portion). In such a case as well, the region where a negative pressure is to be generated by the negative-pressure-generating unit includes at least part of the squeezable tube H. Therefore, after the priming step, microbubbles remaining in the squeezable tube H can be discharged smoothly and assuredly. Furthermore, in such a case, microbubbles adhered to the blood inlet 3a of the dialyzer 3 also inflate under the negative pressure generated by the negative-pressure-generating unit and merge together to form larger bubbles. Such bubbles can therefore be discharged easily.

As illustrated in FIG. 20, the extracorporeal circulation apparatus may include the level-adjusting pump 17 connected to the venous-pressure-measuring unit P at a predetermined position of the blood circuit (the venous blood circuit 2) and that adjusts the liquid surface at the predetermined position. Furthermore, the negative-pressure-generating unit may be formed of the level-adjusting pump 17, and the rollers 14 of the blood pump 4 and the electromagnetic valve V2 both serving as the closing portions. As illustrated in the drawings, the level-adjusting pump 17 is attached to the atmosphere release line Lf extending from the venous-pressure-measuring unit P. The level-adjusting pump 17 adjusts the liquid surface by discharging air from the air layer formed in the venous-pressure-measuring unit P to the outside through the atmosphere release line Lf (in the present embodiment, air in the chamber portion of the venous-pressure-measuring unit P is all discharged so that no air layer is formed).

Thus, in the negative-pressure-generating step S3, as illustrated in FIG. 20, while the blood pump 4 is stopped, the level-adjusting pump 17 is activated with the electromagnetic valves (V2 and V4) being closed and the electromagnetic valve V1 being open, whereby a negative pressure can be generated in the region filled with the priming solution (the region represented by a bold line in the drawing). In this case, the closing portion of the negative-pressure-generating unit is formed of the rollers 14 of the blood pump 4 in the stopped state, and the electromagnetic valve V2.

To summarize, if the extracorporeal circulation apparatus includes the level-adjusting pump 17 and if the negative-pressure-generating unit includes the level-adjusting pump 17 and the closing portion (the rollers 14 of the blood pump 4 and the electromagnetic valve V2) with which the region of the blood circuit that is filled with the priming solution is closed, the generation of a negative pressure in the region filled with the priming solution can be achieved with the use of the level-adjusting pump 17, which is necessary for adjusting the liquid surface.

While some embodiments have been described above, the present invention is not limited thereto. The priming step may be any other type of step, as long as the priming solution supplied through the priming-solution supply line Ld is discharged through the discharge unit (such as the overflow line Le, or the distal end of the arterial blood circuit 1 or the venous blood circuit 2) while a flow route in the blood circuit is filled with the priming solution.

The priming-solution supply line Ld according to the present embodiment is connected at one end thereof to the dialysate introduction line La and allows the dialysate as the priming solution to be supplied to the blood circuit when the electromagnetic valve V4 is open. Alternatively, for example, one end of the priming-solution supply line Ld may be connected to a storage bag storing a physiological saline solution so that the physiological saline solution as the priming solution can be supplied to the blood circuit. As another alternative, the priming-solution supply line Ld may be omitted. In such a case, for example, the dialysate (the priming solution) in the dialysate introduction line La may be filtered (back-filtered) through the purification membranes (in the present embodiment, the hollow fiber membranes) in the dialyzer 3 before being supplied to the blood circuit (the arterial blood circuit 1 and the venous blood circuit 2).

In addition, the priming solution may be another liquid different from dialysate or a physiological saline solution. While the above embodiments are each applied to a dialysis apparatus intended for dialysis treatment, the present invention may also be applied to another apparatus (such as a blood purification apparatus or a plasma adsorption apparatus intended for hemodiafiltration, hemofiltration, or AFBF) that purifies a patient's blood while causing the blood to extracorporeally circulate.

The present invention is applicable to any extracorporeal circulation apparatus and any method of discharging bubbles therefrom that are of any other type or for any other use, as long as the following are executed: a priming step in which a priming solution is discharged through a discharge unit while a flow route in a blood circuit is filled with the priming solution; a negative-pressure-generating step in which, after the priming step, a negative pressure is generated by a negative-pressure-generating unit in the region filled with the priming solution; and a discharge step in which bubbles in the region subjected to the negative pressure generated in the negative-pressure-generating step are caused to flow and are discharged through the discharge unit. Note that the concept of the extracorporeal circulation apparatus includes a blood purification apparatus.

Furthermore, the region filled with the priming solution refers to the entirety or part of a portion of the blood circuit that is filled with the priming solution.

REFERENCE SIGN LIST 1 arterial blood circuit
2 venous blood circuit
3 dialyzer (blood purifier)
4 blood pump (negative-pressure-generating unit)
5 air-trap chamber
6 arterial bubble-detecting unit
7 venous bubble-detecting unit
8, 9 blood identifier
10 duplex pump
11 ultrafiltration pump
12 stator
12a fitting recess
13 rotor
14 roller (squeezing unit)
15 guide pin
16 holding portion
17 level-adjusting pump (negative-pressure-generating unit)
P venous-pressure-measuring unit
H squeezable tube
E control unit
La dialysate introduction line
Lb dialysate drain line
Lc bypass line
Ld priming-solution supply line
Le overflow line
Lf atmosphere release line

The invention claimed is:

1. An extracorporeal circulation apparatus comprising:
 a blood circuit including an arterial blood circuit and a venous blood circuit whose proximal ends are connected to a blood purifier, the blood circuit allowing a patient's blood to extracorporeally circulate from a distal end of the arterial blood circuit to a distal end of the venous blood circuit;
 a discharge unit through which a priming solution supplied into the blood circuit is discharged to an outside;
 a negative-pressure-generating unit that generates a negative pressure in a region of the blood circuit, the region being filled with the priming solution; and
 a control unit that controls the negative-pressure-generating unit,
 wherein the control unit executes
 a priming step in which the priming solution supplied into the blood circuit is discharged through the discharge unit while a flow route in the blood circuit is filled with the priming solution;
 a negative-pressure-generating step in which, after the priming step, a negative pressure is generated in the region by the negative-pressure-generating unit; and
 a discharge step in which bubbles in the region subjected to the negative pressure generated in the negative-pressure-generating step are caused to flow and are discharged through the discharge unit.

2. The extracorporeal circulation apparatus according to claim 1, further comprising a blood pump that delivers liquid by squeezing, with a roller, a squeezable tube connected to the arterial blood circuit, wherein the region where a negative pressure is to be generated by the negative-pressure-generating unit includes at least part of the squeezable tube.

3. The extracorporeal circulation apparatus according to claim 2, wherein the negative-pressure-generating unit includes the blood pump and a closing portion, the closing portion being configured to close the region of the blood circuit that is filled with the priming solution.

4. The extracorporeal circulation apparatus according to claim 1, further comprising a level-adjusting pump connected to a predetermined position of the blood circuit and that adjusts a liquid surface at the predetermined position, wherein the negative-pressure-generating unit includes the level-adjusting pump and a closing portion, the closing portion being configured to close the region of the blood circuit that is filled with the priming solution.

5. The extracorporeal circulation apparatus according to claim 1, wherein the venous blood circuit is provided with an air-trap chamber connected thereto, and wherein the discharge unit is formed of an overflow line extending from a top of the air-trap chamber.

6. The extracorporeal circulation apparatus according to claim 1, wherein the discharge unit is formed of the distal end of the arterial blood circuit or the distal end of the venous blood circuit.

7. The extracorporeal circulation apparatus according to claim 2, further comprising a level-adjusting pump connected to a predetermined position of the blood circuit and that adjusts a liquid surface at the predetermined position, wherein the negative-pressure-generating unit includes the level-adjusting pump and a closing portion, the closing portion being configured to close the region of the blood circuit that is filled with the priming solution.

8. A method of discharging bubbles from an extracorporeal circulation apparatus, the apparatus including
 a blood circuit including an arterial blood circuit and a venous blood circuit whose proximal ends are connected to a blood purifier, the blood circuit allowing a patient's blood to extracorporeally circulate from a distal end of the arterial blood circuit to a distal end of the venous blood circuit;
 a discharge unit through which a priming solution supplied into the blood circuit is discharged to an outside; and
 a negative-pressure-generating unit that generates a negative pressure in a region of the blood circuit, the region being filled with the priming solution, the method comprising:
- a priming step in which the priming solution supplied into the blood circuit is discharged through the discharge unit while a flow route in the blood circuit is filled with the priming solution;
- a negative-pressure-generating step in which, after the priming step, a negative pressure is generated in the region by the negative-pressure-generating unit; and
- a discharge step in which bubbles in the region subjected to the negative pressure generated in the negative-pressure-generating step are caused to flow and are discharged through the discharge unit.

9. The method of discharging bubbles from the extracorporeal circulation apparatus according to claim 8, wherein the extracorporeal circulation apparatus further includes a blood pump that delivers liquid by squeezing, with a roller, a squeezable tube connected to the arterial blood circuit, and wherein the region where a negative pressure is to be generated by the negative-pressure-generating unit includes at least part of the squeezable tube.

10. The method of discharging bubbles from the extracorporeal circulation apparatus according to claim 9, wherein the negative-pressure-generating unit includes the blood pump and a closing portion, the closing portion being configured to close the region of the blood circuit that is filled with the priming solution.

11. The method of discharging bubbles from the extracorporeal circulation apparatus according to claim 8, wherein the extracorporeal circulation apparatus further includes a level-adjusting pump connected to a predetermined position of the blood circuit and that adjusts a liquid surface at the predetermined position, and wherein the negative-pressure-generating unit includes the level-adjusting pump and a closing portion, the closing portion being configured to close the region of the blood circuit that is filled with the priming solution.

12. The method of discharging bubbles from the extracorporeal circulation apparatus according to claim 8, wherein the venous blood circuit is provided with an air-trap chamber connected thereto, and wherein the discharge unit is formed of an overflow line extending from a top of the air-trap chamber.

13. The method of discharging bubbles from the extracorporeal circulation apparatus according to claim 8, wherein the discharge unit is formed of the distal end of the arterial blood circuit or the distal end of the venous blood circuit.

14. The method of discharging bubbles from the extracorporeal circulation apparatus according to claim 9, wherein the extracorporeal circulation apparatus further includes a level-adjusting pump connected to a predetermined position of the blood circuit and that adjusts a liquid surface at the predetermined position, and wherein the negative-pressure-generating unit includes the level-adjusting pump and a closing portion, the closing portion being configured to close the region of the blood circuit that is filled with the priming solution.

15. The method of discharging bubbles from the extracorporeal circulation apparatus according to claim 9, wherein the venous blood circuit is provided with an air-trap chamber connected thereto, and wherein the discharge unit is formed of an overflow line extending from a top of the air-trap chamber.

16. The method of discharging bubbles from the extracorporeal circulation apparatus according to claim 10, wherein the venous blood circuit is provided with an air-trap chamber connected thereto, and wherein the discharge unit is formed of an overflow line extending from a top of the air-trap chamber.

17. The method of discharging bubbles from the extracorporeal circulation apparatus according to claim 11, wherein the venous blood circuit is provided with an air-trap chamber connected thereto, and wherein the discharge unit is formed of an overflow line extending from a top of the air-trap chamber.

18. The method of discharging bubbles from the extracorporeal circulation apparatus according to claim 9, wherein the discharge unit is formed of the distal end of the arterial blood circuit or the distal end of the venous blood circuit.

19. The method of discharging bubbles from the extracorporeal circulation apparatus according to claim 10, wherein the discharge unit is formed of the distal end of the arterial blood circuit or the distal end of the venous blood circuit.

20. The method of discharging bubbles from the extracorporeal circulation apparatus according to claim 11, wherein the discharge unit is formed of the distal end of the arterial blood circuit or the distal end of the venous blood circuit.

* * * * *